US012805932B2

(12) United States Patent
Girouard et al.

(10) Patent No.: US 12,805,932 B2
(45) Date of Patent: Nov. 24, 2026

(54) ACUTE ASSESSMENT OF CARDIAC ABLATION LESIONS

(71) Applicant: CARDIOFOCUS, INC., Marlborough, MA (US)

(72) Inventors: Steven D. Girouard, Chagrin Falls, OH (US); Krista N. Hagfors, Cold Spring, KY (US); Robert E. Neal, II, Redwood City, CA (US); Quim Castellvi, Barcelona (ES)

(73) Assignee: CARDIOFOCUS, INC., Marlborough, MA (US)

( * ) Notice: Subject to any disclaimer, the term of this patent is extended or adjusted under 35 U.S.C. 154(b) by 197 days.

(21) Appl. No.: 18/712,122

(22) PCT Filed: Nov. 21, 2022

(86) PCT No.: PCT/US2022/050578
§ 371 (c)(1),
(2) Date: May 21, 2024

(87) PCT Pub. No.: WO2023/096859
PCT Pub. Date: Jun. 1, 2023

(65) Prior Publication Data

US 2024/0407836 A1 Dec. 12, 2024

Related U.S. Application Data

(60) Provisional application No. 63/282,521, filed on Nov. 23, 2021.

(51) Int. Cl.
*A61B 18/14* (2006.01)
*A61B 18/00* (2006.01)

(52) U.S. Cl.
CPC .................... *A61B 18/1492* (2013.01); *A61B 2018/00351* (2013.01); *A61B 2018/00577* (2013.01);

(Continued)

(58) Field of Classification Search
CPC ............ A61B 18/1233; A61B 18/1492; A61B 2017/00154; A61B 2018/00351;
(Continued)

(56) References Cited

U.S. PATENT DOCUMENTS 6,572,612 B2 6/2003 Stewart
9,265,557 B2 * 2/2016 Sherman .............. A61B 5/4848
(Continued)

FOREIGN PATENT DOCUMENTS

CN 113558753 A 10/2021
JP 2002535033 A 10/2002
(Continued)

OTHER PUBLICATIONS

International Search Report and Written Opinion in PCT Application No. PCT/US2022/050578, mailed Apr. 7, 2023 (13 pages).
(Continued)

*Primary Examiner* — Michael F Peffley
(74) *Attorney, Agent, or Firm* — Leason Ellis LLP

(57) ABSTRACT

Devices, systems and methods are provided for treating conditions of the heart, particularly the occurrence of arrhythmias, more particularly atrial fibrillation. Therapeutic pulsed electric field energy is delivered to portions the heart to provide tissue modification, particularly to the entrances to the pulmonary veins in the treatment of atrial fibrillation. Such tissue modification creates a lesion or series of lesions which act as a conduction block within the tissue to prevent the transmission of aberrant electrical signals. Cardiovascular lesion analysis systems and methods provide information related to the effectiveness of the treatment during the procedure so as to create an electrical blockade within the heart that will remain durable and effective long-term.

66 Claims, 9 Drawing Sheets

(52) U.S. Cl.
CPC ............... *A61B 2018/00648* (2013.01); *A61B 2018/00672* (2013.01); *A61B 2018/00839* (2013.01); *A61B 2018/00875* (2013.01); *A61B 2018/00892* (2013.01); *A61B 2018/00898* (2013.01)

(58) Field of Classification Search
CPC .......... A61B 2018/00357; A61B 2018/00375; A61B 2018/00577; A61B 2018/00613; A61B 2018/00642; A61B 2018/00648; A61B 2018/00672; A61B 2018/00702; A61B 2018/00738; A61B 2018/00839; A61B 2018/00875; A61B 2018/00892; A61B 2018/00898; A61B 2018/167; A61B 2034/2051; A61B 5/0538; A61B 5/1109; A61B 5/367
See application file for complete search history.

(56) References Cited

U.S. PATENT DOCUMENTS

| | | | | |
|---|---|---|---|---|
| 9,326,814 | B2 * | 5/2016 | He | A61B 18/1492 |
| 10,172,673 | B2 | 1/2019 | Viswanathan et al. | |
| 10,842,561 | B2 | 11/2020 | Viswanathan et al. | |
| 11,389,234 | B1 * | 7/2022 | Viswanathan | A61B 18/1206 |
| 11,432,871 | B2 | 9/2022 | Schweitzer et al. | |
| 11,622,713 | B2 * | 4/2023 | Ben-Haim | A61B 5/0538 606/34 |
| 11,738,200 | B2 | 8/2023 | Viswanathan | |
| 12,070,265 | B2 | 8/2024 | Schweitzer et al. | |
| 2005/0096647 | A1 | 5/2005 | Steinke et al. | |
| 2009/0248012 | A1 | 10/2009 | Maor et al. | |
| 2010/0286626 | A1 | 11/2010 | Petersen | |
| 2011/0082450 | A1 | 4/2011 | Melsky | |
| 2014/0350553 | A1 | 11/2014 | Okuyama | |
| 2016/0135690 | A1 | 5/2016 | Brewster | |
| 2016/0143698 | A1 * | 5/2016 | Garcia | A61B 18/1206 606/34 |
| 2017/0367760 | A1 | 12/2017 | Crozier et al. | |
| 2018/0184982 | A1 | 7/2018 | Basu | |
| 2019/0038348 | A1 | 2/2019 | Koblish | |
| 2019/0038349 | A1 | 2/2019 | Koblish et al. | |
| 2019/0231421 | A1 | 8/2019 | Viswanathan et al. | |
| 2019/0388002 | A1 * | 12/2019 | Bozsak | A61B 5/02007 |
| 2020/0129218 | A1 | 4/2020 | Sliwa et al. | |
| 2020/0163707 | A1 | 5/2020 | Sliwa et al. | |
| 2020/0297415 | A1 | 9/2020 | Marshik et al. | |
| 2021/0077187 | A1 | 3/2021 | Koblish et al. | |
| 2021/0169394 | A1 * | 6/2021 | Chou | A61B 5/367 |
| 2021/0169567 | A1 | 6/2021 | Govari | |
| 2022/0117655 | A1 | 4/2022 | Govari et al. | |
| 2022/0218412 | A1 | 7/2022 | De La Rama et al. | |
| 2022/0218959 | A1 | 7/2022 | Valls et al. | |
| 2022/0296297 | A1 | 9/2022 | Melsky et al. | |
| 2022/0323143 | A1 | 10/2022 | Melsky et al. | |
| 2022/0378498 | A1 | 12/2022 | Zhang et al. | |
| 2023/0052114 | A1 | 2/2023 | Marass et al. | |
| 2023/0172650 | A1 | 6/2023 | Castellvi et al. | |
| 2023/0201533 | A1 | 6/2023 | Huffer et al. | |
| 2024/0315770 | A1 | 9/2024 | Mickelsen | |

FOREIGN PATENT DOCUMENTS

| | | | |
|---|---|---|---|
| JP | 2009522058 | A | 6/2009 |
| JP | 2014514031 | | 6/2014 |
| JP | 2018522612 | A | 8/2018 |
| JP | 2020517355 | A | 6/2020 |
| WO | 2001087173 | A2 | 11/2001 |
| WO | 2016181318 | A1 | 11/2016 |
| WO | 2019133608 | A1 | 7/2019 |
| WO | 2021059943 | A1 | 4/2021 |
| WO | 2021127558 | A1 | 6/2021 |

OTHER PUBLICATIONS

Yavin. "Pulsed Field Ablation Using a Lattice Electrode for Focal Energy Delivery" 529-538. Circulation: Arrhythmia and Electrophysiology. Web. Jun. 2020; pp. 529-538; [Retrieved on Mar. 8, 2023]. Retrieved from the Internet: <url: https://www.ahajournals.org/doi/pdf/10.1161/CIRCEP.120.008580>; pp. 530, 531, 533; Figure 2; DOI:10.1161/CIRCEP.120.008580.

Extended European Search Report in EP Application No. 22899315.0-1113/4436507, mailed Sep. 2, 2025.

Japanese Office action in JP Application No. 2023-555312, mailed Jul. 2, 2025, an English translation attached hereto (14 pages).

Japanese Office action in JP Application No. 2023-560578, mailed Jul. 17, 2025, an English translation attached hereto (10 pages).

Non-Final Office Action in U.S. Appl. No. 17/711,574, mailed Jul. 16, 2025 (17 pages).

International Search Report and Written Opinion in PCT Application No. PCT/US2025/029349, mailed Sep. 9, 2025 (26 pages).

Japanese Office Action (including English translation) issued in App. No. JP2024530447 dated Aug. 17, 2026 (pp. 1-26).

* cited by examiner

ACUTE ASSESSMENT OF CARDIAC ABLATION LESIONS

CROSS-REFERENCE TO RELATED APPLICATIONS

This application is a U.S. National Phase Application under 35 U.S.C. § 371 of International Patent Application No. PCT/US2022/050578, filed on Nov. 21, 2022, which claims priority to and the benefit of U.S. Patent Application No. 63/282,521 filed Nov. 23, 2021, entitled "Acute Assessment of Cardiac Ablation Lesions", all of which are incorporated herein by reference as if expressely set forth in their respective entireties herein.

BACKGROUND

Therapeutic energy can be applied to the heart and vasculature for the treatment of a variety of conditions, including atherosclerosis (particularly in the prevention of restenosis following angioplasty) and atrial fibrillation. Atrial fibrillation is the most common sustained cardiac arrhythmia, and severely increases the risk of mortality in affected patients, particularly by causing stroke. In this phenomenon, the heart is taken out of normal sinus rhythm due to the production of erroneous electrical impulses. Atrial fibrillation is thought to be initiated in the myocardial sleeves of the pulmonary veins (PVs) due to the presence of automaticity in cells within the myocardial tissue of the PVs. Pacemaker activity from these cells is thought to result in the formation of ectopic beats that initiate atrial fibrillation. PVs are also thought to be important in the maintenance of atrial fibrillation because the chaotic architecture and electrophysiological properties of these vessels provides an environment where atrial fibrillation can be perpetuated. Thus, destruction or removal of these aberrant pacemaker cells within the myocardial sleeves of the PVs has been a goal and atrial fibrillation is often treated by delivering therapeutic energy to the pulmonary veins. However, due to reports of PV stenosis, the approach has been conventionally modified to one that targets PV antra to achieve conduction block between the PVs and the left atrium. The PV antra encompass, in addition to the pulmonary veins, the left atrial roof and posterior wall and, in the case of the right pulmonary vein antra, a portion of the interatrial septum. In some instances, this technique offers a higher success rate and a lower complication rate compared with pulmonary vein ostial isolation.

Thermal ablation therapies, especially radiofrequency (RF) ablation, are currently the "gold standard" to treat atrial fibrillation by localized tissue necrosis. Typically, RF ablation is used to create a ring of ablation lesions around the outside of the ostium of each of the four pulmonary veins. RF current causes desiccation of tissue by creating a localized area of heat that results in discrete coagulation necrosis. The necrosed tissue acts as a conduction block thereby electrically isolating the veins.

Despite the improvements in reestablishing sinus rhythm using available methods, both success rate and safety are limited by the thermal nature of these procedures. Complications include pulmonary vein stenosis, phrenic nerve injury, esophageal injury, atrio-esophageal fistula, periesophageal vagal injury, perforations, thromboembolic events, vascular complications, and acute coronary artery occlusion, to name a few. Thus, while keeping the technique in clinical practice, safer and more versatile methods of removing or replacing abnormal tissue have been used, such as pulsed electric field therapy (PEF). However, since PEF therapy has a different cellular effect on the tissue, the tissue reacts differently than when receiving RF ablation. Most notably, cells undergoing PEF treatments have altered ability to maintain intra- and extra-cellular concentration gradients. This can result in death of the cell, invoking fibroplastic effects comparable to wound healing, or the cell can recover over the course of minutes to hours or longer. In both cases, the ability for excitable tissue such as cardiomyocytes to conduct action potentials is at least initially compromised and the cells are rendered inexcitable. Unfortunately, it is not readily detectable to determine which regions of cells will maintain this compromise. One cannot distinguish at the time of a therapeutic PEF procedure tissue that is experiencing a change in electrical conduction and contractility as a temporary effect versus tissue that will ultimately die via necrosis or programmed cell death over the course of seconds to tens of hours. Consequently, the conventional cues based on RF energy that physicians monitor throughout an ablation procedure are largely inapplicable and can lead to misleading acute results and inferior chronic results, such as an incomplete block of the aberrant electrical rhythms. Determination of acute ablation success has remained a challenging problem for the treatment of cardiac arrhythmias with all ablation methods. Data from multiple clinical trials on the long-term freedom from arrhythmia for patients confirm that a high percentage of patients are ineffectively treated during their initial procedure. Early atrial fibrillation recurrence rates still range between 50-70%. Better techniques for predicting lesion durability and procedure success during an ablation procedure need to be established. At least some of these objectives will be met by the systems, devices and methods described herein.

SUMMARY OF THE INVENTION

Described herein are embodiments of apparatuses, systems and methods for treating target tissue, particularly cardiac tissue. Likewise, the invention relates to the following numbered clauses:

1. A cardiovascular lesion analysis system comprising:
   an instrument configured to measure at least one voltage value of at least a portion of a cardiovascular lesion;
   an algorithm that evaluates the at least one voltage value so as to determine durability of the at least a portion of the cardiovascular lesion, wherein the at least a portion of the cardiovascular lesion is created by pulsed electric field ablation; and
   a feedback system that conveys the durability.
2. A system as in clause 1, wherein the at least one voltage value comprises at least one pre-ablation voltage value and at least one post-ablation voltage value and wherein the algorithm evaluates the at least one voltage value by determining a representative voltage reduction value from the difference between the at least one pre-ablation voltage value and at least one post-ablation voltage value, and wherein the algorithm determines the likelihood of durability based on the representative voltage reduction value.
3. A system as in clause 2, wherein the algorithm compares the representative reduction value to a threshold voltage reduction value above which the lesion is considered durable so as to determine durability.
4. A system as in any of clauses 2-3, wherein the pre-ablation voltage value is at least 0.1 volts.
5. A system as in any of clauses 2-4, wherein the pre-ablation voltage value comprises an average of individual pre-ablation voltage values and the post-ablation voltage value comprises an average of individual post-ablation voltage values.

6. A system as in clause 5, wherein each of the individual pre-ablation voltage values are at least 0.1 volts.

7. A system as in any of clauses 3-6, wherein the representative voltage reduction value is represented as a percentage of the pre-ablation voltage value.

8. A system as in clause 7, wherein the threshold voltage reduction value is 89%.

9. A system as in clause 7, wherein the threshold voltage reduction value falls within a range of 89-100%.

10. A system as in clause 3-9, wherein the threshold voltage reduction value has at least a 95% confidence level.

11. A system as in any of clauses 3-10, wherein the threshold voltage reduction value is dependent on a baseline voltage value.

12. A system as in clause 11, wherein the threshold voltage reduction value varies in discrete steps in relation to the baseline voltage value.

13. A system as in clause 11, wherein the threshold voltage reduction value varies continuously in relation to the baseline voltage value.

14. A system as in clause 11, wherein the threshold voltage reduction value varies with confidence level.

15. A system as in any of the above clauses, wherein the feedback system conveys the durability as a continuous variable that changes over time.

16. A system as in clause 15, wherein the continuous variable is conveyed as percent reduction in voltage.

17. A system as in clause 16, wherein the feedback system additionally conveys a target percent reduction in voltage.

18. A system as in any of the above clauses, wherein any of the instrument, algorithm and/or feedback system is integral with an electroanatomic mapping system.

19. A system as in any of the above clauses, wherein the feedback system is integrated with a pre-existing visual map provided by the electroanatomic mapping system.

20. A system as in any of the above clauses, wherein the feedback system conveys the durability by providing an alert.

21. A system as in clause 20, wherein the alert comprises a visual alert.

22. A system as in clause 21, wherein the visual alert comprises a color code indicating durability or a level of durability.

23. A system as in clause 21, wherein the visual alert comprises at least one letter, word, number and/or symbol indicating durability or a level of durability.

24. A system as in clause 21, wherein the alert comprises an auditory alert.

25. A system as in any of clauses 21-24, wherein the alert is binary.

26. A system as in any of clauses 21-24, wherein the alert is gradated.

27. A system as in any of the above clauses, wherein the feedback system comprises a map illustrating an anatomical location of the at least a portion of the cardiovascular lesion.

28. A system as in clause 27, wherein the feedback system comprises an indicator of the durability of the at least a portion of the cardiovascular lesion at the anatomical location on the map.

29. A system as in any of the above clauses, wherein the feedback system conveys the durability to a user in real-time as the instrument moves.

30. A system as in any of the above clauses, wherein the instrument is configured to deliver the pulsed electric field energy.

31. A system as in clause 30, wherein the instrument comprises an electrode through which the pulsed electric field energy is delivered and wherein the electrode is configured to be positioned against or adjacent tissue to create the at least a portion of the cardiovascular lesion.

32. A system as in clause 31, wherein the at least a portion of the cardiovascular lesion is formed from a single application of the electrode against or adjacent the tissue, and wherein the algorithm determines a location for a next single application of the electrode.

33. A system as in clause 32, wherein the location for the next single application of the electrode overlaps the at least a portion of the cardiovascular lesion formed from the single application of the electrode.

34. A system as in any of clauses 32-33, wherein the location for the next single application of the electrode provides sufficient overlap of stun zones between kill zones to form a continuous durable lesion.

35. A system as in any of the above clauses, wherein the pulsed electric field energy leaves extracellular matrices of the cardiovascular lesion intact.

36. A system as in any of the above clauses, wherein the pulsed electric field energy comprises a series of packets, wherein each packet comprises biphasic pulses.

37. A system for determining lesion placement comprising:

a catheter having an electrode configured to deliver pulsed electric field energy toward cardiovascular tissue so as to generate a lesion, wherein a first lesion is generated by delivering the pulsed electric field energy toward the cardiovascular tissue at a first location;

an algorithm that determines a second location for a second lesion based on a determined durability of the first lesion; and a feedback system that conveys the second location.

38. A system as in clause 37, wherein the determined durability of the first lesion is generated by the algorithm by comparing a representative reduction value to a threshold voltage reduction value above which the first lesion is considered durable.

39. A system as in clause 38, wherein the representative voltage reduction value is calculated as a differential between a pre-ablation voltage value and a post-ablation voltage value.

40. A system as in clause 39, wherein the pre-ablation voltage value is at least 0.1 volts.

41. A system as in clause 39, wherein the pre-ablation voltage value comprises an average of individual pre-ablation voltage values and the post-ablation voltage value comprises an average of individual post-ablation voltage values.

42. A system as in clause 41, wherein each of the individual pre-ablation voltage values are at least 0.1 volts.

43. A system as in any of clauses 39-42, wherein the representative voltage reduction value is represented as a percentage of the pre-ablation voltage value.

44. A system as in clause 43, wherein the threshold voltage reduction value is 89%.

45. A system as in clause 43, wherein the threshold voltage reduction value falls within a range of 89-100%.
46. A system as in any of clauses 43-45, wherein the threshold voltage reduction value has at least a 95% confidence level.
47. A system as in any of clauses 37-46, wherein the impedance of the cardiovascular tissue remains below a threshold corresponding to impedance generated by thermal ablation.
48. A system as in any of clauses 37-47, wherein the pulsed electric field energy comprises a series of packets, wherein each packet comprises biphasic pulses.
49. A cardiovascular lesion analysis system comprising:
a catheter having at least one electrode; and
a pulsed electric field generator connectable with the catheter, wherein the pulsed electric field generator includes an algorithm configured to deliver at least one dose of pulsed electric field energy through at least one of the at least one electrode to an area of cardiovascular tissue so as to create a lesion and to measure at least one voltage value of at least a portion of a cardiovascular lesion through at least one of the at least one electrode, and wherein the algorithm determines durability of the at least a portion of the cardiovascular lesion with the use of the at least one voltage value.
50. A system as in clause 49, wherein the at least one voltage value comprises a representative voltage reduction value, and wherein the algorithm compares the representative reduction value to a threshold voltage reduction value above which the lesion is considered durable so as to determine durability.
51. A system as in clause 50, wherein the representative voltage reduction value is represented as a percentage of a pre-ablation voltage value.
52. A system as in clause 51, wherein the threshold voltage reduction value is 89%.
53. A system as in clause 51, wherein the threshold voltage reduction value falls within a range of 89-100%.
54. A system as in any of clauses 51-53, wherein the pre-ablation voltage value is at least 0.1 volts.
55. A system as in any clauses 51-53, wherein the pre-ablation voltage value comprises an average of individual pre-ablation voltage values.
56. A system as in clause 55, wherein each of the individual pre-ablation voltage values are at least 0.1 volts.
57. A system as in any of clauses 50-56, wherein the threshold voltage reduction value has at least a 95% confidence level.
58. A system as in any of clauses 49-57, wherein the pulsed electric field energy leaves extracellular matrices of the cardiovascular lesion intact.
59. A system as in any of clauses 49-58, wherein the pulsed electric field energy comprises a series of packets, wherein each packet comprises biphasic pulses.
60. A system as in any of clauses 49-59, wherein the algorithm provides the durability to a visual map that includes the area of cardiovascular tissue.
61. A system as in clause 60, wherein the visual map is provided by an electroanatomic mapping system.
62. A system as in any of clauses 60-61, wherein the visual map illustrates an anatomical location of the at least a portion of the cardiovascular lesion.
63. A system as in clause 62, wherein the feedback system comprises an indicator of the durability of the at least a portion of the cardiovascular lesion at the anatomical location on the map.
64. A system as in any of clauses 49-63, wherein the algorithm provides the durability as an alert.
65. A system as in clause 64, wherein the alert comprises a visual alert.
66. A system as in clause 65, wherein the visual alert comprises a color code indicating durability or level of durability.
67. A system as in clause 65, wherein the visual alert comprises at least one letter, word, number and/or symbol indicating durability or level of durability.
68. A system as in clause 64, wherein the alert comprises an auditory alert.
69. A system as in any of clauses 64-68, wherein the alert is binary.
70. A system as in any of clauses 64-68, wherein the alert is gradated.
71. A method of evaluating durability of a lesion in cardiovascular tissue of a patient comprising:
delivering at least one dose of pulsed electric field energy to an area of the cardiovascular tissue so as to create the lesion;
determining a representative voltage reduction value for the lesion; and
determining durability of the lesion by comparing the representative reduction value to a threshold voltage reduction value above which the lesion is considered durable.
72. A method as in clause 71, wherein the representative voltage reduction value is calculated as a differential between a pre-ablation voltage value and a post-ablation voltage value.
73. A method as in clause 72, wherein the pre-ablation voltage value is at least 0.1 volts.
74. A method as in clause 72, wherein the pre-ablation voltage value comprises an average of individual pre-ablation voltage values and the post-ablation voltage value comprises an average of individual post-ablation voltage values.
75. A method as in clause 74, wherein each of the individual pre-ablation voltage values are at least 0.1 volts.
76. A method as in clause 71, wherein the representative voltage reduction value is represented as a percentage of the pre-ablation voltage value.
77. A method as in clause 76, wherein the threshold voltage reduction value is 89%.
78. A method as in clause 76, wherein the threshold voltage reduction value falls within a range of 89-100%.
79. A method as in clause 71, wherein the threshold voltage reduction value has at least a 95% confidence level.
80. A method as in clause 71, wherein the lesion comprises a portion of an overall lesion.
81. A method as in clause 80, wherein the overall lesion has a ring shape.
82. A method as in clause 81, wherein the ring shape surrounds least one entrance to a pulmonary vein.
83. A method as in clause 80, wherein the overall lesion has a linear shape.
84. A method as in clause 83, wherein the linear shape forms a cavo-tricuspid isthmus line.

85. A method as in clause 71, wherein delivering at least one dose of pulsed electric field energy is achieved by positioning an electrode near or against the area of the cardiovascular tissue.
86. A method as in clause 85, wherein the electrode is positioned against the area with at least 10 grams of contact force.
87. A method as in clause 85, wherein the electrode has continuous solid surface positionable near or against the area of the cardiovascular tissue so that the lesion has a disc shape.
88. A method as in clause 71, further comprising delivering at least one additional dose of pulsed electric field energy to the lesion if the representative reduction value is below the threshold voltage reduction value.
89. A method as in clause 71, wherein the determining step is accomplished within approximately 30 minutes of the delivering step.
90. A method as in clause 71, wherein the pulsed electric field energy is below a threshold for inducing coagulative thermal damage in the cardiovascular tissue.
91. A method as in clause 71, wherein the pulsed electric field energy comprises a series of packets, wherein each packet comprises biphasic pulses.
92. A method as in clause 90, wherein each packet has a length of up to 1 second.
93. A method as in clause 71, wherein the threshold voltage reduction value depends on a baseline voltage value.
94. A method as in clause 93, wherein the threshold voltage reduction value varies continuously in relation to the baseline voltage value.
95. A method as in clause 93, wherein the threshold voltage reduction value varies in steps in relation to the baseline voltage value.
96. A method as in clause 93, wherein the threshold voltage reduction depends on a confidence level.
97. A method as in clause 71, wherein the threshold voltage reduction value is determined from a voltage reduction value threshold curve.
98. A method of generating a durable lesion in cardiovascular tissue of a patient comprising:

delivering a dose of pulsed electric field energy to an area of the cardiovascular tissue;

determining a voltage reduction value for the area of the cardiovascular tissue after delivering the dose; and delivering one or more additional doses of pulsed electric field energy to the area of the cardiovascular tissue until the voltage reduction value is at least 89% which forms the durable lesion.

99. A method as in clause 98, wherein determining the voltage reduction value comprises determining a representative pre-ablation voltage value in the area of the cardiovascular tissue prior to the delivering of the dose the voltage reduction value, determining a representative post-ablation voltage value in the area of the cardiovascular tissue after delivering the dose of the voltage reduction value, and calculating a differential between the representative pre-ablation voltage value and the representative post-ablation voltage value.

100. A method as in clause 99, wherein the representative pre-ablation value is at least 0.1 mV.
101. A method as in clause 99, wherein the representative pre-ablation voltage value comprises an average of pre-ablation voltage values and/or the representative post-ablation voltage value comprises an average of post-ablation voltage values.
102. A method as in clause 98, wherein the durable lesion comprises a plurality of overlapping doses.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Devices, systems and methods are provided for treating conditions of the heart, particularly the occurrence of arrhythmias, more particularly atrial fibrillation. The devices, systems and methods deliver therapeutic energy to portions the heart to provide tissue modification, particularly to the entrances to the pulmonary veins in the treatment of atrial fibrillation. Such tissue modification creates a lesion or series of lesions which act as a conduction block within the tissue to prevent the transmission of aberrant electrical signals. Generally, the tissue modification systems include a specialized treatment catheter, a high voltage waveform generator and at least one distinct energy delivery algorithm. Additional accessories and equipment are also utilized, particularly an electroanatomic mapping (EAM) system. EAM systems allow operators to generate anatomic geometry of the heart and record intracardiac electrical activation in relation to specific anatomic locations within the heart by capturing measured electrical signal metrics (intensity, delay of signal arrival from a distant stimulus, etc). Thus, the EAM technology allows one to accurately determine the location of arrhythmia origin, define cardiac chamber geometry in three dimensions, delineate areas of anatomic interest, and allow catheter manipulation and positioning without fluoroscopic guidance. In addition, devices, systems and methods described herein provide information related to the effectiveness of the treatment during the procedure so as to create an electrical blockade within the heart that will remain durable and effective long-term. In some instances, the devices, systems and methods described herein evaluate characteristics of targeted tissue at a desired level of specificity, such as within a single lesion (e.g. so as to identify differing zones of treatment effects within the lesion which may in turn be utilized to determine where to create additional lesions), of a single lesion (e.g. so as to identify if a single lesion is likely to remain durable over time), or within a contiguous series of lesions (e.g. so as to identify gaps between lesions or insufficient areas along a lesion path or blockade), to name a few. Such devices, systems and methods may utilize, at least in part, features provided by EAM technology. In some instances, the EAM information is generated with the use of a mapping catheter and in other instances this is achieved with technology built into the specialized treatment catheter. For ease of discussion, embodiments having the technology combined into the specialized treatment catheter will be provided but are not so limited.

Figure 1:
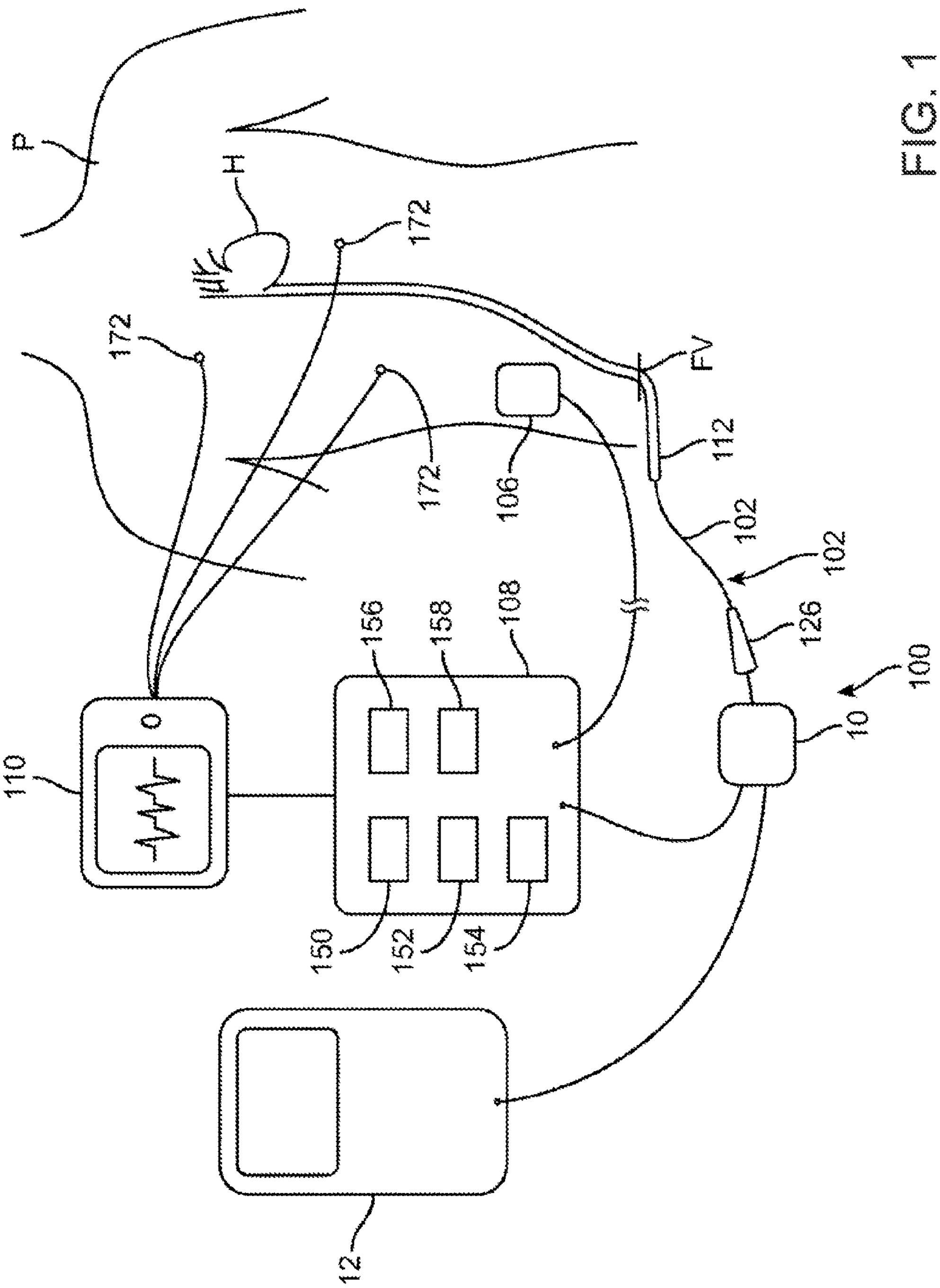
FIG. 1 illustrates an embodiment of a tissue modification system.

FIG. 1 illustrates an example tissue modification system 100. In this embodiment, the tissue modification system 100 includes a specialized catheter 102, a high voltage waveform generator 108 and at least one distinct energy delivery algorithm 152. In this embodiment the generator 108 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, however any other suitable energy storage element may be used. In addition, one or more communication ports are included. In this embodiment, an external cardiac monitor 110 is included and connected to external electrodes 172 which are applied to the patient P to acquire the ECG. In this embodiment, the treatment catheter 102 is designed to be monopolar, wherein the distal end of the catheter 102 has at least one delivery electrode and a return electrode 106 is positioned upon the skin outside the body, typically on the thigh, lower back or back. In this embodiment, the heart H is accessed via the right femoral vein FV by a suitable access procedure, such as the Seldinger technique. Typically, an introducer sheath 112 is inserted into the femoral vein FV which acts as a conduit through which various catheters and/or tools may be advanced, including the treatment catheter 102. The distal end of the catheter 102 is advanced through the inferior vena cava, through the right atrium, through a transseptal puncture, and into the left atrium so as to access the entrances to the pulmonary veins. In this embodiment, the catheter 102 is used to perform cardiac mapping which refers to the process of identifying the temporal and spatial distributions of myocardial electrical potentials during a particular heart rhythm. Cardiac mapping during an aberrant heart rhythm aims at elucidation of the mechanisms of the heart rhythm, description of the propagation of activation from its initiation to its completion within a region of interest, and identification of the site of origin or a critical site of conduction to serve as a target for treatment. Once the desired treatment locations are identified, the catheter 102 is utilized to deliver the treatment energy.

Embodiments illustrated herein include a catheter 102 having a delivery electrode 122 that is shown as a "solid tip" electrode having a cylindrical shape with a distal face having a continuous surface. In some embodiments, the cylindrical shape has a diameter across its distal face of approximately 2-3 mm and a length along the shaft 120 of approximately 1 mm, 2 mm, 1-2 mm, 3 mm, 4 mm, 3-4 mm, 5 mm, 6 mm, 7 mm, 8 mm, 9 mm, 10 mm, etc. It may be appreciated that such electrodes are typically hollow yet are referred to as solid due to visual appearance. Likewise, such electrodes may include holes for irrigations flow and/or mechanical flexibility. Energy is provided to the catheter 102, and therefore to the delivery electrode 122, via a cable 130 that is connectable to the generator 108. The energy is delivered in a sequence, such as the repeated application of energy in point-by-point fashion, such as around a pulmonary vein to create a circular treatment zone or along a line, etc. This is considered "focal therapy". It may be appreciated that a variety of other catheter 102 designs may be utilized. In some embodiments, the catheters 102 are designed to deliver "one shot" therapy. One shot therapy is considered to be a therapy wherein the energy is delivered via the delivery electrode to the entire circumference of the entrance to the pulmonary vein in a "one shot" singular delivery of energy, however such delivery may be repeated if desired. Thus, the electrode 122 often has a loop or flower shape. The electrode 122 may optionally be reapplied; rotation of the electrode 122 may occur between "shots" if desired.

Additional example embodiments of energy delivery catheters 102 configured to provide focal therapy are provided in international patent application number PCT/US2018/067504 titled "OPTIMIZATION OF ENERGY DELIVERY FOR VARIOUS APPLICATIONS" which claims priority to Provisional Patent Application No. 62/610,430 filed Dec. 26, 2017 and U.S. Provisional Patent Application No. 62/693,622 filed Jul. 3, 2018, all of which are incorporated herein by reference for all purposes. In another example, in some embodiments, the energy delivery catheter 102 may have a variety of end effectors such as according to Provisional Patent Application 63/159,331 titled "DEVICES FOR THE DELIVERY OF PULSED ELECTRIC FIELDS IN THE TREATMENT OF CARDIAC TISSUE" filed Mar. 10, 2021, all of which are incorporated herein by reference for all purposes. Likewise, treatment energy may be delivered with a variety of catheter designs, optionally with the use of a variety of accessories, such as according to international patent application number PCT/US2020/066205 titled "TREATMENT OF CARDIAC TISSUE WITH PULSED ELECTRIC FIELDS", filed Dec. 18, 2020 which claims priority to Provisional Patent Application No. 62/949,633 filed Dec. 18, 2019, Provisional Patent Application No. 63/000,275 filed Mar. 26, 2020 and Provisional Patent Application No. 63/083,644 filed Sep. 25, 2020, all of which are incorporated by reference for all purposes.

In the embodiment of FIG. 1, the proximal end of the treatment catheter 102 is electrically connected with an interface connector 10 which is electrically connected with the waveform generator 108 and a separate external device 12, such as one having the capability of providing the electroanatomic mapping procedure (e.g. a CARTO® system, EnSite™ system, RHYTHMIA HDX™ system, KODEX-EPD system, AcQMap™ system, etc.). The interface connector 10 minimizes any potential interference between the various pieces of equipment connected to the contacts (e.g. electrodes, sensors, etc.) of the cardiac treatment catheter. However, it may be appreciated that in some embodiments the treatment catheter 102 is directly connected to the generator 108, external device 12 and/or other device. In addition, in this embodiment the generator 108 is connected with an external cardiac monitor 110 to allow coordinated delivery of energy with the cardiac signal sensed from the patient P.

Figure 2:
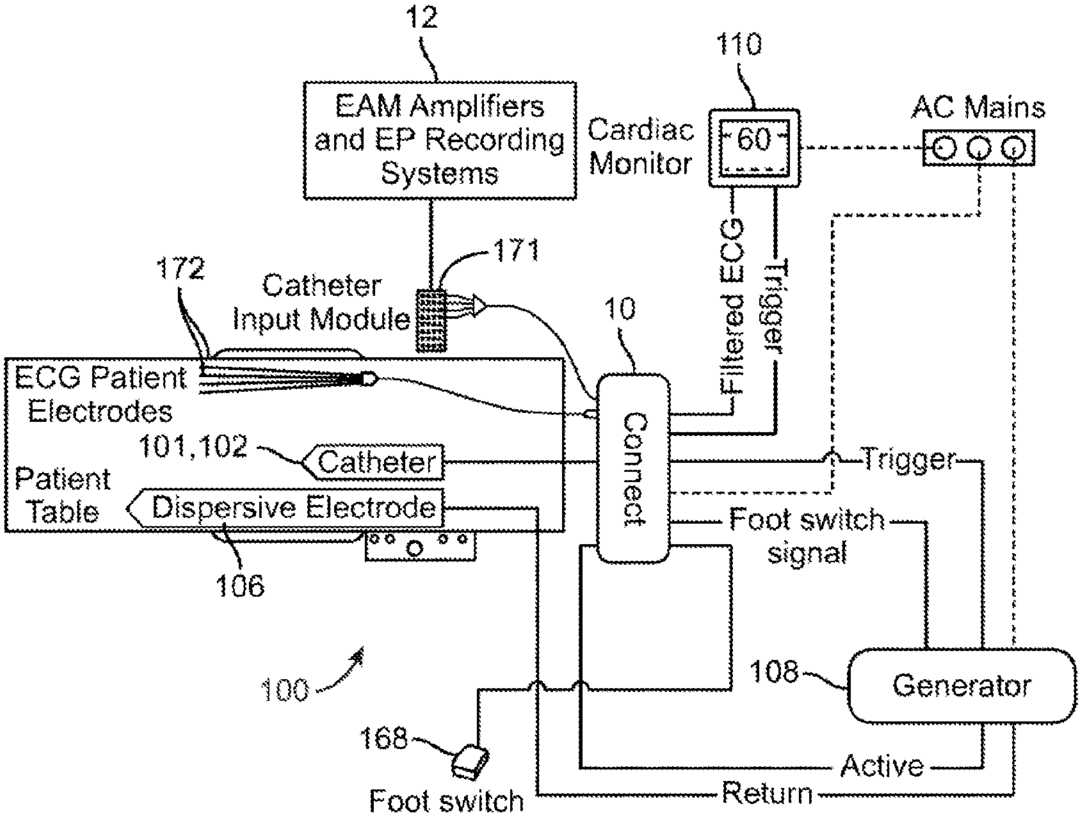
FIG. 2 provides a schematic illustration of a similar tissue modification system.

It may be appreciated that in some instances the interface connector 10 is connected directly to an electroanatomic mapping system, such as to a patient interface unit of the electroanatomic mapping system, with the use of a cable. However, it may also be appreciated that in other embodiments, the interface connector 10 is connected to a pin box, break out box, input-output box, junction box or other input module 171 that is then connected to the electroanatomic mapping system, such as with a specialized cable, as illustrated in FIG. 2. The specialized cable spreads the multi-cable line into individual component connectors or tip pins that are insertable into receptacles in the pin box. This allows access to each electrode individually. The pin box is then connected to the electroanatomic mapping system. It may also be appreciated that the interface connector 10 may include features of the pin box so as to eliminate a separate pin box. Thus, the interface connector 10 may include receptacles for receiving tip pins and the associated electronics.

Example EAM systems include CARTO® systems by Biosense Webster/Johnson & Johnson, EnSite™ systems by St. Jude Medical/Abbott, KODEX-EPD systems by Philips, AcQMap systems by Acutus Medical and Rhythmia HDX™ systems by Boston Scientific, to name a few. The CARTO mapping system is one of the most widely used mapping systems and will be used herein for example. The CARTO mapping system utilizes a low-level magnetic field delivered from three separate coils in a locator pad beneath the patient. The magnetic field strength from each coil is detected by a location sensor embedded proximal to the tip of a specialized treatment catheter. The strength of each coil's magnetic field measured by the location sensor is inversely proportional to the distance between the sensor and coil. Hence, by integrating each coil's field strength and converting this measurement into a distance, the location sensor (and therefore, catheter tip location) can be triangulated in space. The specialized treatment catheter typically includes proximal and distal electrode pairs, and a tip electrode capable of treatment energy delivery. The catheter can be moved along a surface of the heart to record local endocardial activation times for arrhythmia mapping, while simultaneously recording location points to generate 3D chamber geometry. CARTO provides accurate representation of chamber geometry and the capability of generating isochronal activation maps and playable propagation maps. It also has the capability to record locations of important anatomic landmarks (e.g. the bundle of His), areas of electrical scar (e.g. to create voltage/scar maps) and vessels (e.g. coronary sinus, pulmonary veins). CARTO also allows recording of ablation lesion location facilitating creation of ablation lines.

Prior to arrhythmia mapping, a stable location reference is established. This is accomplished by placing the location magnet, a triangular apparatus containing three magnetic coils, beneath the patient and table. The location of this magnet is aligned anywhere inside a defined circumference at the start of the procedure. A reference patch is affixed to the patient's back roughly overlying the cardiac chamber of interest. Should the location reference magnet or patch become displaced during the procedure, their original location is recorded by CARTO to allow proper repositioning. This allows for accurate tracking of mapping catheter position, consistency of anatomic landmark and ablation lesion locations, and precise reconstruction of chamber geometry.

Once the location reference has been stably situated, an appropriate timing reference and window is selected. The timing reference is any selected recording, such as intracardiac electrogram (EGM) or surface ECG lead, representative of activation of the chamber of arrhythmia origin. Intracardiac EGMs are often selected as the timing reference as these are generally more consistent in appearance and precise in timing than surface ECG recordings, and consequently, are more reliable. Any component of the reference electrogram may be chosen for a timing reference, including maximum (peak positive) deflection, minimum (peak negative) deflection, maximum upslope (dV/dT) or maximum downslope. In addition to using an electric signal metric based on a timing within the incoming signal, the time delay for the electrical signal itself to reach the location of interest from a natural or induced electrical propagation event may also be measured.

In addition to facilitating activation mapping, the EAM system provides location mapping features capable of recording sites of anatomic relevance, areas of low endocardial voltage representing scar, and areas of ablation. Ablation causes a variety of cellular reactions, as will be described in more detail herein, ranging from stunning to dying and death. Cardiomyocytes in each of these stages do not conduct electricity almost immediately after ablation. Stunned cardiomyocytes recover and will regain the ability to conduct electricity, a process that occurs over minutes to hours or longer. Dead and dying cardiomyocytes will cease to conduct electricity over the long term. Over the 1-4 weeks following ablation, the dead cells are removed by the body and replaced by scar tissue, and the accumulated dead zones are used to create durable conduction blockades. Targeted specific anatomic locations include the superior vena cava, inferior vena cava, right pulmonary vein, left pulmonary vein, right atrium, right atrial appendage, left atrium, left atrial appendage, right ventricle, left ventricle, right ventricular outflow tract, left ventricular outflow tract, ventricular septum, left ventricular summit, regions of myocardial scar, myocardial infarction border zones, myocardial infarction channels, ventricular endocardium, ventricular epicardium, papillary muscles and the purkinje system, to name a few. Treatments are delivered at isolated sites or in a connected series of treatments. Types of treatment include the creation of left atrial roof line, left atrial posterior/inferior line, posterior wall isolation, lateral mitral isthmus line, septal mitral isthmus line, left atrial appendage, right sided cavotricuspid isthmus (CTI), pulmonary vein isolation, superior vena cava isolation, vein of Marshall, lesion creation to target Complex Fractionated Atrial Electrograms (CFAE), lesion creation to target Focal Impulse and Rotor Modulation (FIRM), and targeted ganglia ablation. Such tissue modification creates a conduction block within the tissue to prevent the transmission of aberrant electrical signals.

In the embodiments described herein, the tissue modification is achieved with the use of pulsed electric field energy, examples of which are provided herein in later sections. Pulsed electric fields (PEFs) are provided by the generator 108 and delivered to the tissue through a delivery electrode 122 placed on or near the targeted tissue area within the heart H. The one or more energy delivery algorithms 152 specify electric signals which provide the PEF energy delivered to the cardiac tissue which cause cell death by non-thermal effects (e.g. energy below a threshold for thermal ablation; below a threshold for inducing coagulative thermal damage; below a threshold damage to extracellular matrices, etc.) reducing or avoiding inflammation, and/or preventing denaturation of stromal proteins in the anatomical structures, particularly at sensitive sites implicated in treatment morbidity or mortality, such as the phrenic nerve, esophagus, and vasculature (e.g. preventing stricture). Thus, the delivery of energy to target tissue causes little or no destruction of critical anatomy, such as tissue-level architectural proteins among extracellular matrices thereby leaving the extracellular matrices intact. It may be appreciated that the non-thermal energy is also not cryogenic (i.e. it is above a threshold for thermal damage caused by freezing). Thus, the temperature of the target tissue remains in a range between a baseline body temperature (such as 35° C.-37° C. but can be as low as 30° C.) and a threshold for thermal ablation. Thus, targeted ranges of tissue temperature include 30-65° C., 30-60° C., 30-55° C., 30-50° C., 30-45° C., 30-35° C. Thus, lesions in the heart tissue are not created by thermal injury as the temperature of the tissue remains below a threshold for thermal ablation (e.g. 65° C.). In addition, the impedance of the tissue typically remains below a threshold generated by thermal ablation. Charring and thermal injury of tissue changes the conductivity of the heart tissue. This increase in impedance/reduction in conductivity often indicates thermal injury and reduces the ability of the tissue to receive further energy. In some instances, the impedance of the system circuit from the cathode to the anode remains in the range of 25-250 Ω, 50-200Ω or 75-125Ω during delivery of PEF energy. In general, the algorithms 152 are tailored to affect tissue to a pre-determined depth and/or volume and/or to target specific types of cellular responses to the energy delivered.

A variety of different electric signals can be used to generated PEF energy. Such signals are typically characterized by the amount of time that energy is continuously delivered. Continuous energy delivery can lead to thermal damage. Therefore, PEF energy is not continuous and is delivered in packets. Each energy packet comprises a series of high voltage pulses separated by a rest period. Typically, a series of packets is delivered to create a lesion. Packet length may vary but is typically up to one second. In some embodiments, packet length is up to 0.5 seconds, up to 0.1 seconds or up to 1 millisecond. Such signals are also characterized by a variety of additional parameters which will be described in more detail in later sections.

Figure 3:
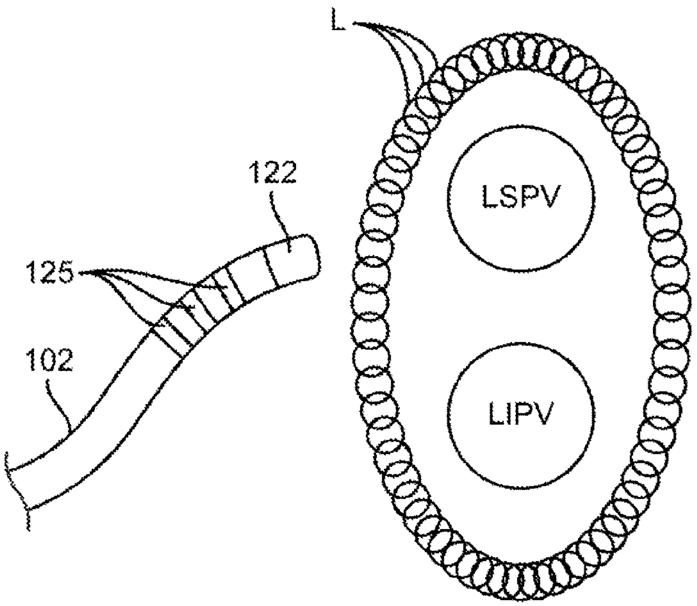
FIG. 3 illustrates an example of treating tissue in a point-by-point fashion with the use of the treatment catheter.

As mentioned, in some embodiments, tissue modification is achieved by treating tissue in a point-by-point fashion with the use of the treatment catheter 102. FIG. 3 illustrates a treating the tissue surrounding the opening of the left superior pulmonary vein LSPV and left inferior pulmonary vein LIPV in a point-by-point fashion with the use of the treatment catheter 102 (with assistance of mapping) to create an oval shaped treatment zone of overlapping lesions L around the pulmonary veins LSPV, LIPV. The catheter 102 includes a delivery electrode 122 and in some embodiments the catheter 102 includes one or more additional electrodes 125 (e.g. ring electrodes) positioned along the shaft 120 proximal to the delivery electrode 122. In some embodiments, some or all of the additional electrodes can be used for stimulating and recording (for electrophysiological mapping), so a separate cardiac mapping catheter is not needed when using catheter 102 for lesion creation, or for other purposes such as sensing, etc.

During treatment, physicians look at several cues to determine where they should treat next in the point-by-point sequence. For example, a physician may consider impedance measurements, electrogram signals, mapping system placement (e.g., distances measured relative to prior treatment delivery sites marked, fluoroscopy, etc). In the field of radiofrequency ablation, known protocols are often followed, such as the CLOSE protocol. However, such protocols are inapplicable to PEF energy delivery and would erroneously direct the physician to utilize lesion placements that would result in gaps in the intended ablation region and therefore failed conduction block and treatment failure. This is often due to the transient effects of energy delivery in portions of the lesion, considered a "stun" effect to the cells.

As mentioned previously, when creating a lesion L using PEF energy, a portion of the cells receiving the energy will be killed by the PEF therapy, ultimately replacing the tissue with transmural fibrotic scar. And, another portion of the tissue will be stunned by the PEF therapy, acutely experiencing a marked decrease in electrical conduction (i.e., "stunned") but ultimately recovering from the PEF injury. The stunning phenomenon is likely the result of a penumbral band of injured, but not killed cells in the region surrounding lethally affected tissue. The injured cells lose their ability to maintain concentration gradients between their intracellular and extracellular environments due to a temporary disruption in their membrane integrity. This temporarily eliminates their ability to be excited by neighboring cells and their ability to passively conduct electrical signals to adjacent excitable cells. This effect may have pronounced implications on clinical outcomes by confounding the ability to accurately determine intraprocedural treatment efficacy. To ensure durable clinical efficacy from PEF cardiac ablation procedures, it is important to ensure that the acute electrical isolation is not reliant on the stunned tissue, but instead reflects the killed tissue that will result in a durable fibrotic scar. Thus, the stun effect has the potential to result in "false positive" electrical isolation outcomes for cardiac ablation procedures.

Figure 4:
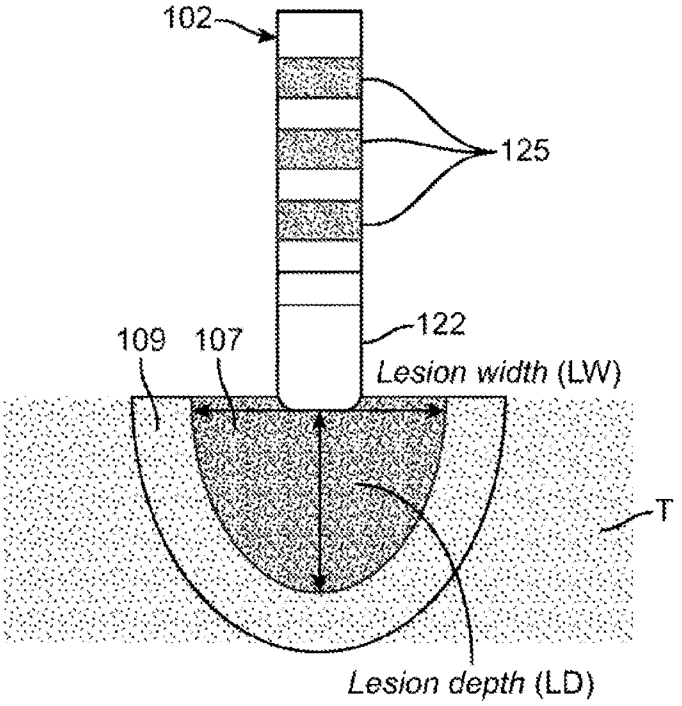
FIG. 4 illustrates a lesion having a killed zone and a stun zone.

FIG. 4 illustrates a lesion L having a killed zone 107 and a stun zone 109. The PEF energy typically creates these zones of treatment extending radially outwardly from the delivery electrode 122. As shown, a zone closest to the delivery electrode 122 (i.e. zone 107) endures immediate or eventual cell death via initiated programmed cell death mechanisms, and the surrounding zone (i.e. zone 109) is stunned and may not lead to enduring or permanent cell death.

A variety of measures have been undertaken to identify boundaries of stunned and killed areas. In some instances, a swine heart model has been utilized. A 7F catheter with a 3.5 mm ablation electrode (TactiCath, Abbott) was connected to a pulsed electric field (PEF) generator (CENTAURI, Galaxy Medical) and positioned in the right ventricle RV and left ventricle LV under EnSite guidance in two closed chest pigs. Biphasic PEF current was delivered between the ablation electrode and a skin patch at 13 RV sites (28 Amp, total pulse width of 1.4 ms, 4 pulses) and 19 LV sites (35 Amp, 1.6 ms, 7 pulses). Two hours after ablation, triphenyl tetrazolium chloride (TTC, a marker for mitochondrial activity) was administered. Pigs were sacrificed and hearts were excised and fixed in formalin. Hearts were sectioned and stained with hematoxylin and eosin (H&E) and Masson trichrome. Cytochrome c oxidase (COX) staining was also performed to examine mitochondrial activity to delineate stun and kill lesion boundaries.

Ablation lesions were well demarcated with TTC staining, showing a dark central zone surrounded by pale boundaries. Histology showed destruction of myocyte architecture within the pale boundaries. A hyperstained (dark red) rim beyond the pale boundaries indicated the stun zone. COX staining showed no or low mitochondrial activity within the pale boundary, consistent with an ablated region. Enhanced activity of COX staining extended to unaffected normal myocardium, consistent with the stun zone. This region is consistent with a hyperstained red rim of TTC around the ablation zone. This increased mitochondrial activity results from cells that were injured from the PEF and are undergoing reparative processes to recover from this injury, using ATP (e.g., increased $Na^{+}$-$K^{+}$ pump activity to restore appropriate electrolyte concentration gradients) in the process. These extra energy demands require upregulated mitochondrial activity. Therefore, acute ventricular lesions produced by PEF ablation show clear demarcation by TTC staining. COX staining suggests that killed portions of the lesions are surrounded by a zone that is actively undergoing recovery from the cellular injury, indicative of a stun zone (temporary cell injury interrupting cell electrical conduction and contractility).

Further, studies were undertaken to evaluate the temporal evolution of voltage signal changes in response to focal PEF protocols to determine the recovery pattern for stunned tissue versus killed tissue. Preclinical animal laboratory studies characterized the temporal evolution of the stun effect to determine if there was a predictable rate of treatment size reduction over time. Such preclinical studies are used to ensure adequate treatment overlap of lesions created clinically to compensate for the presence of stunned tissue and to select optimal follow-up timepoints to evaluate acute efficacy.

In one of these preclinical animal laboratory studies, a porcine model was used wherein a plurality of sites within the heart were targeted with PEF energy and voltage signals were measured at particular time intervals with a conventional EAM system. At the start of the study, the porcine heart chamber was voltage mapped with the EAM system. Then, locations for PEF energy delivery were defined on the EAM system to keep adequate space between lesions. Spheres of 8 mm size and centered on the proposed PEF delivery locations were defined on the EAM system. Using a treatment catheter and targeting 10 g of contact force, focal lesions were created within the heart chamber at each proposed location. Ablation parameters and separation distances were used that provided distinct non-overlapping lesions. In this study, four treatment sites were generated, one in each of the four cardiac chambers. Each heart chamber was then remapped so that voltage measurements were taken from the endocardial surface of each chamber at locations in and around where PEF energy was applied.

In addition, a cavo-tricuspid isthmus (CTI) line was created. Linear ablation of the inferior vena cava-tricuspid isthmus has become the standard treatment for typical atrial flutter. In the animal study, the treatment catheter was repeatedly placed and a series of PEF activations were delivered with 3 mm spacing of EAM markers along the CTI, generating a line of isolation. Using mapping and/or treatment catheters, the temporal delay between points on opposite sides of the CTI ablation line was measured to verify a blockade of energy transmission therethrough.

Serial voltage remapping was undertaken to determine the temporal evolution of voltage measurements from approximately 5 min to over 5 hours post-PEF treatment. In addition, adenosine testing was utilized to determine whether the voltage map changes in response. Adenosine was delivered in increasing increments (6, 12, 18, . . . mg) until AV block was reached, while generating a voltage map at a given focal site. Following adequate map generation at the targeted site, time was allowed for the heart to recover from the adenosine challenge before moving to the next focal lesion, where the voltage map during adenosine challenge was repeated at the new site. This process was repeated for each focal lesion.

The targeted tissues were then explanted from the heart. The heart-lungs complex was infused with saline solution using the natural vasculature (aorta to coronary arteries) with 500 ml, heparinized NaCl solution. After flushing, the heart-lungs complex was be infused with 500 ml formalin at 10% for 1 hour to preserve the anatomical shape during fixation. After a minimum of 2-days of formalin fixation, the heart was opened to measure the ablation lesions grossly and to process the tissues for histological evaluation.

It may be appreciated that a reduction in measured voltage during a voltage map signifies a reduction in energy transmission as regions targeted by ablation express reduced excitability. This is the desired outcome when making a lesion. During the serial remaps, the size of the region of voltage amplitude reduction became smaller over the course of time up to and beyond at least one hour post-treatment. This resolution of reduced voltage amplitude size over time indicated a clear "stunning" effect was occurring at least along the perimeter of the lesion wherein stunned tissue was shown to be recovering over time. Because the size of the region of voltage amplitude reduction continued to become smaller over at least one hour, it was shown that the timing of the conventional remap at 20 min post ablation to confirm adequate ablation cannot accurately confirm that the ablated tissue has durable chronic voltage reduction. The duration associated with voltage amplitude recovery was correlated with the distance from the delivered lesion, whereby the most distant regions recovered the most quickly, followed progressively by voltage recovery closer to the ultimate lesion as time evolved. This indicates a correlation between treatment intensity (since treatment intensity decays exponentially away from the tissue-electrode interface for PEF delivery) and electrogram voltage recovery.

Because stun effect recovery occurs over the time-scale of at least hours, conventional acute interoperative assessments of lesion durability developed for thermal ablation methods cannot be relied upon to guide treatments using PEF energy. Doing so would subject a user to erroneously consider certain regions or connected lesions to be effectively ablated wherein they are in fact reversibly affected, stunned tissue. This error may lead to gaps in the formation of a chronic contiguous transmural scar needed for conduction blockade, resulting in isolation lesions that are not durable and may result in the eventual recurrence of arrhythmia symptoms.

Here, methods, systems, and devices are provided that account for this stunning effect and provide reliable acute interoperative assessments of lesion durability so that long-term complete conduction blocks can be achieved. In one embodiment, methods, systems and devices are provided for interoperative assessment of a contiguous series of individual lesions in the creation of an electrical blockade (e.g. overall lesion) to ensure that such blockade is durable long term. In this embodiment, a tissue modification system 100 is utilized to deliver therapeutic PEF energy to portions the heart, such as to create a ring of lesions L around the entrances to pulmonary veins such as illustrated in FIG. 3, as in the treatment of atrial fibrillation. Such tissue modification is intended to create a conduction block within the tissue to prevent the transmission of aberrant electrical signals. In this embodiment, voltage maps are generated with the use of an EAM system before and after creation of the lesions L. Such voltage maps provide a plurality of voltage values for locations along and around the lesions L. Thus, a set of pre-ablation voltage values are generated, and a set of post-ablation voltages are generated for a variety of locations.

Figure 5:
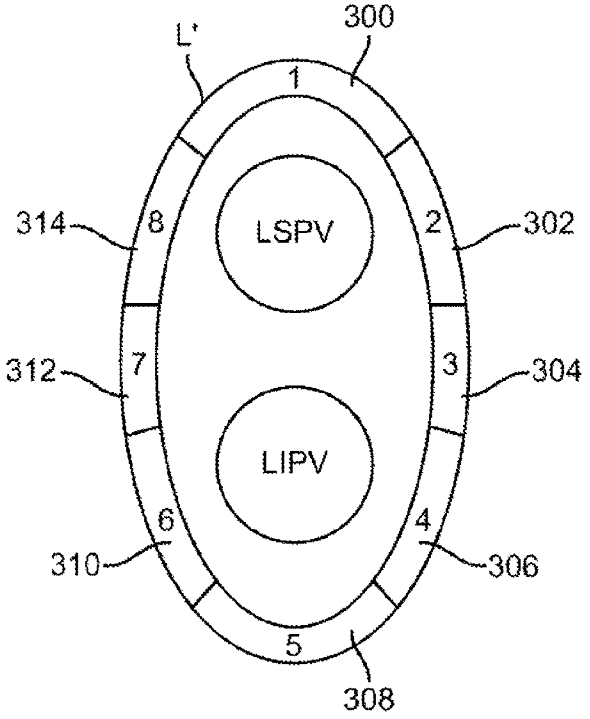
FIG. 5 illustrates a continuous ring of lesions split into sections, formed around the left superior pulmonary vein and the left inferior pulmonary vein.

FIG. 5 illustrates a continuous ring of lesions L' representing the individual lesions of FIG. 3 formed around the left superior pulmonary vein LSPV and the left inferior pulmonary vein LIPV. In this embodiment, the ring of lesions L' is split into a plurality of sections, such as 8 sections as illustrated in FIG. 4. Here, the plurality of sections comprises a first section 300, a second section 302, a third section 304, a fourth section 306, a fifth section 308, a sixth section 310, a seventh section 312, and an eight section 314. An area is defined within each section that includes at least three anatomical points having both pre-ablation voltage values and post-ablation voltage values. Thus, the anatomical points are chosen due to their ability to be correlated in the pre-ablation voltage map and the post-ablation voltage map. In this embodiment, the anatomical points are chosen wherein the pre-ablation voltage is above a minimal activity threshold, such as 0.1 mV or 0.2 mV. At a given anatomical point, the differential between the pre-ablation voltage value and the post-ablation voltage value is determined and considered the voltage reduction value at that anatomical point. In this embodiment, the voltage reduction value is expressed as a percent reduction in voltage between the pre-ablation voltage value and the post-ablation voltage value. Next, in this embodiment, the voltage reduction value at each of the three anatomical points are gathered and the median value is considered the representative voltage reduction value. If the representative voltage reduction value is less than 89%, the section is considered to contain at least one lesion L that is not durable. Therefore, the desired representative voltage reduction value for durability is greater than or equal to 89%, including 89%, at least 89%, 90%, at least 90%, 91%, at least 91%, 92%, at least 92%, 93%, at least 93%, 94%, at least 94%, 95%, at least 95%, 96%, at least 96%, 97%, at least 97%, 98%, at least 98%, 99%, at least 99%, 100%. Due to identification of the section, at least a portion of the section can be re-treated during the procedure to avoid reversal of the lesion formation over time. Retreatment can be performed after analysis of a section, a plurality of sections or all of the sections. It may be appreciated that the process can be repeated as many times as desired until each section is deemed durable. Once this process is completed, the entire ring of lesions L' is considered durable and electrical blockade complete.

It may be appreciated that any number of anatomical points may be chosen from which to determine the representative voltage reduction value, including one, two, three, four, five, six, seven, eight, nine, ten, 2-5, 3-4, 5-10, at least 3, at least 5, at least 10, etc. It may also be appreciated that a contiguous series of lesions, such as a ring of lesions L', may be divided into any number of sections, including one, two, three, four, five, six, seven, eight, nine, ten, 2-5, 3-4, 6-8, 5-10, at least 3, at least 5, at least 8, at least 10. Likewise, shapes other than rings may be analyzed including lines, arcs, angles, and irregular shapes to name a few. In addition, it may be appreciated that sections may be chosen so that each section includes a single lesion L. In such instances, each lesion L may be evaluated as durable or non-durable rather than a plurality of lesions evaluated at a time.

In the embodiment described above, the threshold of %-reduction of interest was derived using the described representative technique with real-world clinical data analyzing pre- and post-treatment voltage maps, and 90-day retreatment data to derive where inadequate electrical isolation durability was incurred due to the stun effect to tissue (all patients achieved acute electrical conduction block at the time of their procedure). The desired threshold for the representative voltage reduction value of >89% is based on data analysis of the ECLIPSE AF (Atrial Fibrillation) clinical trial data. The ECLIPSE AF clinical trial was undertaken by Galaxy Medical, Inc. (San Carlos, CA) to evaluate catheter ablation of atrial fibrillation using Pulsed Electric Field (PEF) ablation with the CENTAURI™ System (e.g. generator 108) connected to a CE-Marked focal, contact force sensing catheter (e.g. treatment catheter 102). The multi-center study included patients that were undergoing first-time catheter ablation for paroxysmal atrial fibrillation (PAF) or persistent atrial fibrillation (PerAF) of short-duration (<1 year). Data included voltage mapping measurements pre-ablation and post-ablation. Durability of lesions were checked during a 90-day remapping. The analysis included 160 sections that were defined and measured as described above. A statistical analysis yielded a sensitivity of 97.9% and a positive predictive power of 98.6% ($p<0.05$) for an optimal voltage reduction value threshold of 88.7% (89%). Thus, this analysis had a high sensitivity rate and a high predictive power.

Example voltage mapping data is provided in Table 1 for lesions in a patient; note, values of X indicate insufficient data for calculation. Here, a ring of lesions L' was analyzed around the left pulmonary veins LPV and another ring of lesions L' was analyzed around the right pulmonary veins RPV. Each ring of lesions L' was split into eight sections. Voltage reduction as a percentage was calculated by dividing the post-treatment voltage by the pre-treatment voltage at the same approximate location. The median voltage reduction value is shown along with its corresponding pre-ablation and post-ablation voltage values.

TABLE 1

Example voltage mapping data for a patient.

| Section (LPVs) | Pre-Ablation Voltage (mV) | Post-Ablation Voltage (mV) | Voltage reduction value (%) | Section (RPVs) | Pre-Ablation Voltage (mV) | Post-Ablation Voltage (mV) | Voltage reduction value (%) |
|---|---|---|---|---|---|---|---|
| 1 | 2.66 | X | | 1 | 2.81 | 0.07 | 97.51% |
| 2 | 2.03 | 0.23 | 88.67% | 2 | 1.07 | 0.08 | 92.52% |
| 3 | 3.12 | 0.07 | 97.76% | 3 | 2.12 | 0.12 | 94.34% |
| 4 | 2.45 | 0.44 | 82.04% | 4 | X | X | |
| 5 | 3.74 | 0.12 | 96.79% | 5 | 3.97 | 0.12 | 96.98% |
| 6 | 2.35 | 0.07 | 97.02% | 6 | 3.48 | 0.14 | 95.98% |

TABLE 1-continued

Example voltage mapping data for a patient.

| Section (LPVs) | Pre-Ablation Voltage (mV) | Post-Ablation Voltage (mV) | Voltage reduction value (%) | Section (RPVs) | Pre-Ablation Voltage (mV) | Post-Ablation Voltage (mV) | Voltage reduction value (%) |
|---|---|---|---|---|---|---|---|
| 7 | 2.06 | 0.06 | 97.09% | 7 | 3.05 | 0.07 | 97.70% |
| 8 | 3.77 | 0.08 | 97.88% | 8 | 3.59 | 0.12 | 96.66% |

Figure 6A:
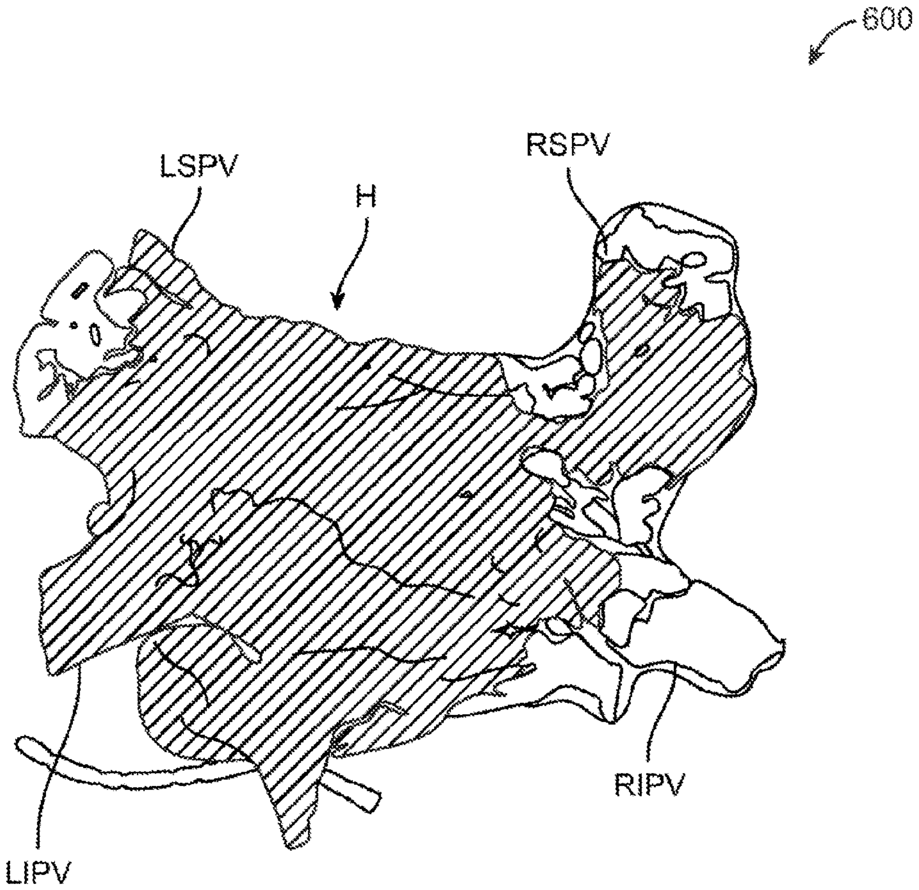
FIGS. 6A-6C illustrate voltage maps for the patient of Table 1.
Figure 6B:
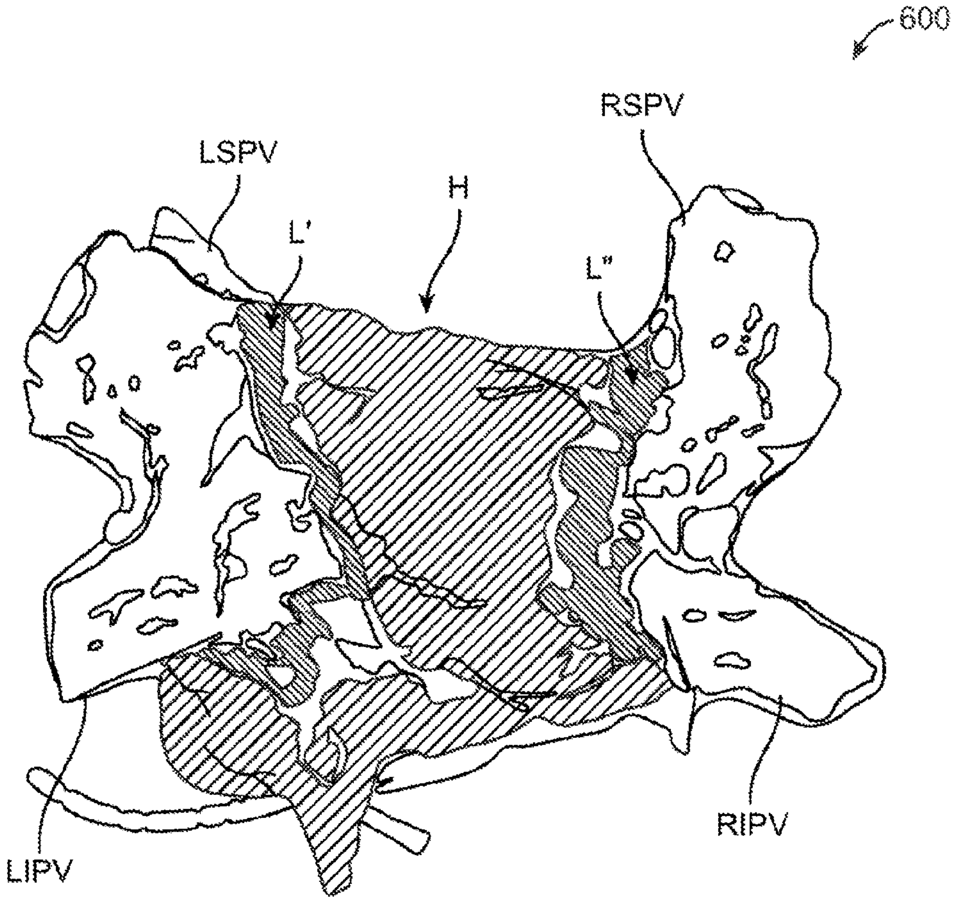
Figure 6C:
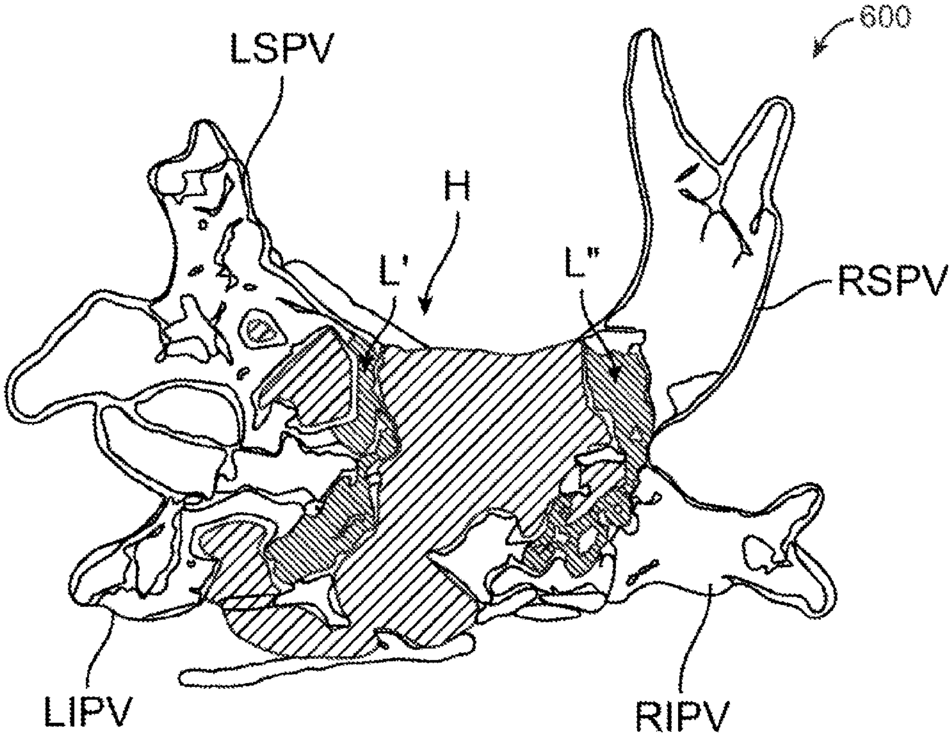

FIGS. 6A-6C illustrate voltage maps for the patient of Table 1. FIG. 6A is a voltage map 600 taken prior to treatment. The voltage map is a three-dimensional rendering of the anatomy of the heart H from its posterior side. Thus, the left superior pulmonary vein LSPV and left inferior pulmonary vein LIPV are visible on the left and the right superior pulmonary vein RSPV and right inferior pulmonary vein RIPV are visible on the right. Typically, such voltage maps are colored wherein gray areas correspond to inexcitable tissue (electrogram amplitudes <0.2 mV), purple areas correspond to normal voltage amplitude (electrogram amplitudes >0.5 mV), red/yellow colors depict areas with reduced (low) electrogram voltage amplitudes (electrogram amplitudes 0.2-0.5 mV). Here, purple areas are represented by hatch marks and extend over the surfaces of the heart H into each of the pulmonary veins LSPV, LIPV, RSPV, RIPV. Treatment for this patient included the generation of a ring of lesions L' around the left pulmonary veins LPV and another ring of lesions L" around the right pulmonary veins RPV (as indicated by double hatch marks), in a manner such as illustrated in FIG. 3. FIG. 6B is a voltage map of the same patient and a similar view of the heart taken intraoperatively after treatment. As shown, the rings of lesions L', L" have created an electrical blockade so that the hatch marked area representing purple areas (electrogram amplitudes >0.5 mV) does not extend past the rings of lesions L', L" into the pulmonary veins LSPV, LIPV, RSPV, RIPV. The area on the other side of the lesions L', L" (covering the pulmonary veins LSPV, LIPV, RSPV, RIPV) is gray color representing amplitudes <0.2 mV. FIG. 6C is a voltage map of the same patient and a similar view of the heart H taken 90 days after treatment. As shown, the lesions L" around the right pulmonary veins RSPV, RIPV have maintained the electrical blockade. This is consistent with the data presented in Table 1 wherein the voltage reduction values for each of the eight sections around the right pulmonary veins was above 89%. Thus, all of the lesions were durable. However, the lesions L' around the left pulmonary veins LSPV, LIPV have not maintained the electrical blockade and the hatch marked regions representing purple areas now extend past the lesions L' into the left pulmonary veins LSPV, LIPV. This is consistent with the data presented in Table 1 wherein the voltage reduction values of section 2 and section 4 were below 89%. Thus, lesions in these sections were not durable long term.

Thus, it may be appreciated that in some instances a target tissue area has one of three general conditions. If a target tissue area has a baseline voltage below a minimal activity threshold, such as 0.1 mV or 0.2 mV, the area is considered inexcitable at the outset. If a target tissue area had a voltage that was above the minimal activity threshold but was treated and then has a voltage reduction value that is at or above a desired voltage reduction value, such as at least 89%, the area is considered to be durably treated. If a target tissue area had a voltage that was above the minimal activity threshold but was treated and then has a voltage reduction value that is below a desired voltage reduction value, such as at least 89%, the area is considered to be non-durably treated and would benefit from re-treatment or supplemental treatment to reach durability.

Figure 7A:
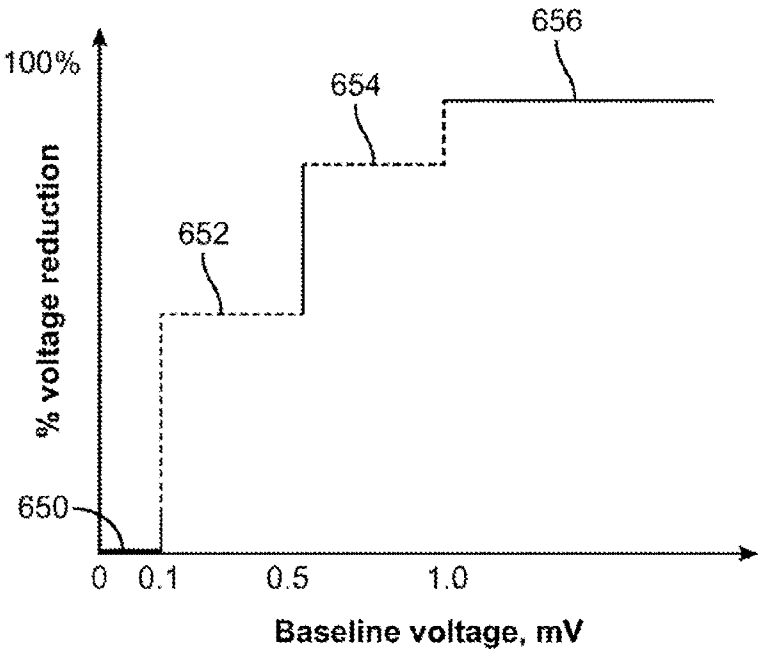
FIGS. 7A-7C illustrate example desired voltage reduction value thresholds varying with example baseline voltage values.
Figure 7B:
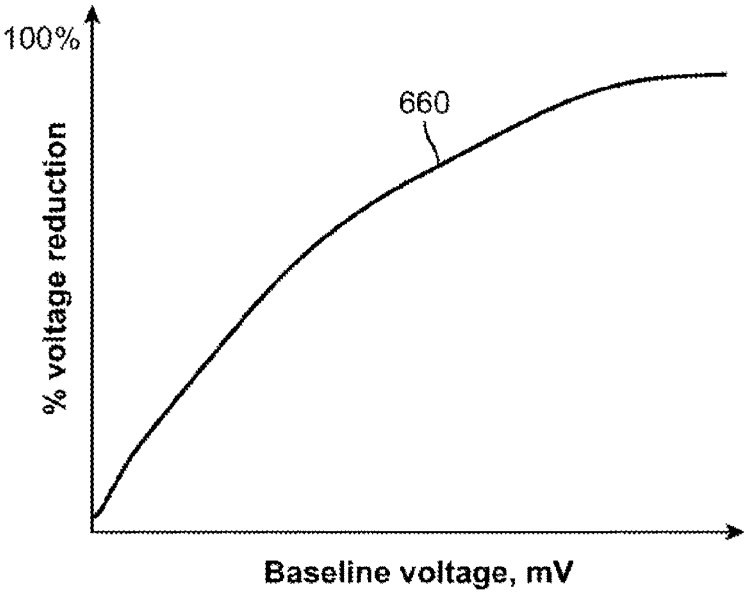
Figure 7C:
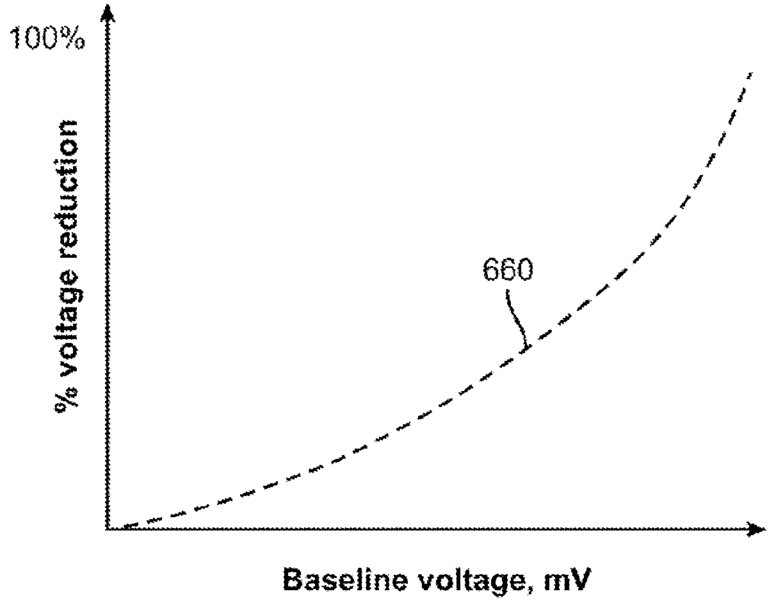

In some embodiments, the desired voltage reduction value varies with the baseline voltage value. For example, in some embodiments, tissue areas that had a moderate baseline voltage at the outset would meet a lower desired voltage reduction value threshold upon treatment for the treatment to be considered durable. For example, FIG. 7A provides a visual illustration of example desired voltage reduction value thresholds varying with example baseline voltage values. Here, four distinct threshold levels are shown: a first threshold level 650 for baseline voltages up to a first baseline voltage value (e.g. 0.1 mV), a second threshold level 652 for baseline voltages between the first baseline voltage value and a second baseline voltage value (e.g. 0.1 mV-0.5 mV), a third threshold level 654 for baseline voltages between the second baseline voltage value and a third baseline voltage value (e.g. 0.5 mV-1.0 mV), a fourth threshold level 656 for baseline voltages between the third baseline voltage value and a fourth baseline voltage value (e.g. over 1.0 mV). In this example, the first threshold level 650 is essentially zero in that the tissue area has met the threshold without treatment since it is considered suitably inexcitable from the outset. In addition, the second threshold level 652 is greater than the first threshold level, the third threshold level 654 is greater than the second threshold level 652 and the fourth threshold level 656 is greater than the third threshold 654 level. It may be appreciated that the number of threshold levels and the value of each threshold level may vary by situation. Likewise, in some embodiments, the desired voltage reduction value varies continuously with the baseline voltage value, rather than in discrete steps. For example, FIGS. 7B-7C provides a visual illustration of example desired voltage reduction value thresholds varying continuously with example baseline voltage values, thus creating desired voltage reduction value threshold curves 660.

Figure 8:
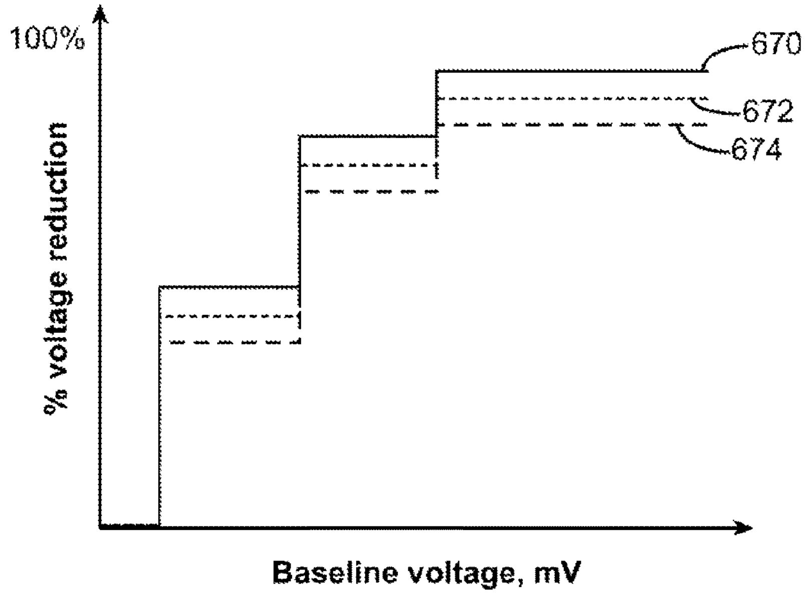
FIG. 8 provides a visual illustration of example desired voltage reduction value thresholds varying with example baseline voltage values including confidence levels.

In other embodiments, each desired voltage reduction value is provided with a confidence value. Therefore, in some embodiments, a desired voltage reduction value can be utilized or chosen based on a desired confidence value or level. For example, the desired voltage reduction values of the embodiments described herein above were based on a high confidence level, such as a 95% confidence level. Such desired voltage reduction values would be used when the circumstances suggest high reliability of durability. However, in some instances, such as in particular tissue types or treatment locations, a lower confidence level may be suitable. In such instances, a lower desired voltage reduction value (e.g. a desired voltage reduction value of less than 89%) may be tolerated to consider a lesion durable. In some embodiments, the user is provided voltage reduction values and/or confidence values during the procedure. This empowers the user with the data and a sense of durability, permitting a degree of user interpretation to determine suitable durability of a lesion based on peripheral data such as the region of the heart, the user's experience, the thickness the heart at this region, or the density and dose of ablation treatments applied in that region, etc. FIG. 8 provides a visual illustration of example desired voltage reduction value thresholds varying with example baseline voltage values, wherein confidence levels are also illustrated. Here, high confidence curve 670 of desired voltage reduction value thresholds varying with example baseline voltage values is shown, such as having a 95% confidence level that durability information is accurate. In addition, a lower confidence curve 672 of desired voltage reduction value thresholds varying with example baseline voltage values is shown, such as having a 90% confidence level that durability information is accurate. Further, a still lower confidence curve 674 of desired voltage reduction value thresholds varying with example baseline voltage values is shown, such as having an 85% confidence level that durability information is accurate. It may be appreciated that these confidence levels could be, for example, based on experimental data or selected as standard deviations from the absolute threshold. Example confidence intervals include 95% confidence, 90% confidence, 85% confidence, or 80% confidence in durability, etc. Such confidence values may be provided to the user in a graphical formal or numerical format, to name a few. Alternatively, a continuous variable level of confidence may be provided to the user. For example, such confidence values may be graphed over time as a user moves an ablation catheter over a region in the heart, or the confidence values may be provided on final voltage maps.

It may be appreciated that in some embodiments the representative voltage reduction value is not expressed as a percent reduction, rather the voltage values are expressed in absolute terms as the voltage values themselves (e.g. in millivolts). In other embodiments, the representative voltage reduction value is instead a target lowest voltage threshold value, such as 0.05 mV, 0.1 mV, 0.2 mV, 0.3 mV, 0.4 mV, 0.5 mV, 0.6 mV, 0.7 mV, 0.8 mV, 0.9 mV, or 1.0 mV, to name a few. In such embodiments, after delivery of one or more PEF treatments, a lesion, section or region of voltage values is generated and compared with the target lowest voltage threshold value. For example, 20 minutes after completing a treatment procedure, the user may generate a voltage map and examine for any regions that exceed the target lowest voltage threshold value. Any region that has a voltage above this target lowest voltage threshold value may be considered stun-affected only. The user may then touch up this region, strategically placing lesions in the undertreated areas to improve confidence in durability of the electrical conduction block in these areas. In some embodiments, the EAM system also highlights specific area where the threshold is not satisfied, helping guide the user where additional treatments are desired.

It may be appreciated that the lesion analysis may be provided to the user in a variety of ways. In some embodiments, the lesion analysis and feedback to the user are provided by analysis systems embedded in an EAM system or by analysis systems that are separate but functions in conjunction with an EAM system, such as with the use of an algorithm that integrates or coordinates with the existing functionality of the EAM system. For example, in some embodiments, lesion analysis (e.g. section analysis) is automatically undertaken during treatment progression with the use of the algorithm so that feedback is provided to the user in real-time throughout the treatment, such as after generation each section of lesions. In such instances, a section is predetermined so that completion of the section is a triggering event. Such predetermination may be built into the algorithm or determined by user input, such as by inputting information such as type of procedure, type of lesion, location of lesion, geometrical positioning of devices such as the treatment catheter, number of activations, time period, or any combination of these, to name a few. When a section is considered a single lesion, completion of the lesion is a triggering event.

In some embodiments, the feedback is provided by an alert, such as visual and/or auditory alert. Example visual alerts include words, such as "complete", "durable" or "transitory". Other visual alerts include numbers or letters, such as D for durable and I for incomplete. Or 1 for durable and 0 for not durable. It may be appreciated that such visual alerts may include at least one letter, word, number and/or symbol, to name a few. In other embodiments, the visual alert comprises a color code indicating durability or level of durability, such as green for durable and red for not durable. Or, gradations of color between durable and not durable indicating how close the lesion is to durability or indicating the confidence level of the durability rating. In some embodiments, the alert is an auditory alert such as a particular sound indicating generation of a durable lesion and optionally a different sound for generation of a lesion that lacks durability. In some embodiments the feedback is binary (e.g. durable/not durable) and in other embodiments the feedback is gradated (such as a durability with a particular confidence level or a indication of how close the lesion is to sufficient durability). In some embodiments, the feedback is provided as a continuous variable (e.g., %-reduction) plotted over time or indicated in a table. If plotted over time, a recommended reference %-reduction value (e.g., 89% reduction, 90% reduction, etc.) may be overlaid, so a user may gain a degree of confidence in the durability of any given voltage reduction region.

In some embodiments, feedback is provided in a manner that is integrated with pre-existing visual maps provided by the EAM system and in other embodiments a separate map or information display is provided regarding the status of the durability of the lesions, such as in each of the sections. In other embodiments, the lesion analysis and feedback are separate from an EAM system and utilize information generated by one or more other devices, such as a generator 108, external cardiac monitor 110, other system accessory, or a combination of these. In such embodiments, lesion analysis may likewise be automatically undertaken during treatment progression with the use of the algorithm so that feedback is provided to the user real-time throughout the treatment, such as after generation each lesion or section of lesions.

It may be appreciated that analysis of the durability of lesions may be similarly undertaken with the use of other data generated from EAM systems or other systems such as generators, cardiac monitors, or accessories. Example parameters for such use include monopolar or bipolar electrogram amplitude reduction (e.g. absolute or %), frequency domain changes (e.g. frequency content, ratio of high:low frequency content, power at a specific frequency or band of frequencies, etc.), local voltage gradient change, absolute voltage change, absolute voltage magnitude, percent reduction voltage amplitude, local gradients of voltage, frequency content, change in local gradient, time domain features (e.g., rise time, measure of fractionation, timing of zero crossings, local conduction delay, duration of waveform elevation beyond a threshold such as 0, etc.), monopolar EGMs, bipolar EGMs, combinations of monopolar and bipolar EGMs, regional analysis by sector, normalization to baseline map, spatial patterns of voltage, spatial patterns of change, dimensions of region of reduced potential, and frequency content, to name a few. It may be appreciated that, in some embodiments, the EAM system or electrogram recording system tracks or indicates the metric of interest relative to a prescribed threshold in real-time as the ablation catheter is moved.

In other embodiments, an EAM system is used to compare information before and after an entire treatment session to check for regions of suspicious durability. In one embodiment, the EAM system plots and displays the voltage maps of pre- and post-treatment (e.g. side-by-side) for the user to visualize regions that experienced stronger or weaker signal reduction. In another embodiment, the EAM system performs mathematical operations between pre- and post-treatment signal metrics. For example, in one embodiment, the EAM system divides captured voltage values on the post-treatment map by the pre-treatment value from the same approximate (or interpolated) location. In this way, a %-reduction EAM map is produced, whereby the user can quickly visualize areas that received strong reductions and weak reductions. Certain threshold criteria, such as 89% voltage reduction, may used by this map, whereby the EAM system flags all regions that do not satisfy the >89% reduction criteria. This gives the user a rapid at-a-glance perspective on the success of the treatment and the anticipated durability of the electrical isolation produced. In some embodiments, if regions do not satisfy the criterion, the user may further follow-up and "touch-up" the targeted regions with additional lesion placements, increasing confidence in the durability of the electrical conduction block.

In another embodiment, pre- and post-treatment maps of the same region may be compared for other signals, such as the absolute voltage reduction, or changes in any other suitable electrical characteristics (e.g. phase, fractionated time domain, etc). These maps may be used in a similar method as described above.

In some embodiments, the elapsed time between the pre-treatment and the post-treatment maps are used to adjust the resulting outcome metrics. This is because some lesions will already begin recovery during the procedure, particularly in cases where significant time is expended to complete a series of point-by-point lesions. The recovery shown by the lesions treated at the beginning of the procedure is expected to be higher than the recovery shown by the lesions treated later in the procedure. Thus, recorded metrics can be scaled in accordance to relative time to result in homogeneous assessment regardless the post-treatment map.

In some embodiments, post-treatment maps are generated at one or more intervals to evaluate the durability of electrical signal reduction following a determined amount of stun recovery time. For example, post-treatment maps may be generated immediately after completing one or more lesions, immediately after completing an entire lesion set, or intervals such as 5, 10, 20, 30, 45, 60, 120, or 180 min post-treatment. For example, a 20 min dwell period may be used prior to performing the post-treatment remap, in this way, the least-affected stunned tissue regions will already be recovering their signal, and so subtler stunned regions may be discovered and visualized with less interference.

As mentioned previously, in some embodiments, lesion analysis is automatically undertaken during treatment progression with the use of the algorithm so that feedback is provided real-time throughout the treatment. In some embodiments, the algorithm utilizes this information to determine a location for a next lesion, such as when performing point-by-point ablation along a ring or line. As mentioned, overlap of lesions is desirable to ensure that gaps are not left between lesions, particularly after stun zone recovery. Thus, the location for the next single application of energy provides sufficient overlap of stun zones between kill zones to form a continuous durable lesion.

In some embodiments, the next application of energy is directed to the same location as the first application of energy. This would be desired when the first application or dose was insufficient for durability. For example, the voltage reduction value may have been below the threshold for durability, such as below 89%. In such instances, additional applications of energy may be provided until the lesion is determined to be sufficiently durable.

As mentioned previously, lesions L and sections of lesions may be analyzed that were generated with the use of PEF energy. In the system 100 shown in FIG. 1, pulsed electric fields (PEFs) are provided by the generator 108 and delivered to the tissue through the delivery electrode 122 placed on or near the targeted tissue area. In some embodiments, high voltage, short duration biphasic electric pulses are delivered through the electrode 122 in the vicinity of the target tissue. These electric pulses are provided by at least one energy delivery algorithm 152. In some embodiments, each energy delivery algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail herein. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 9:
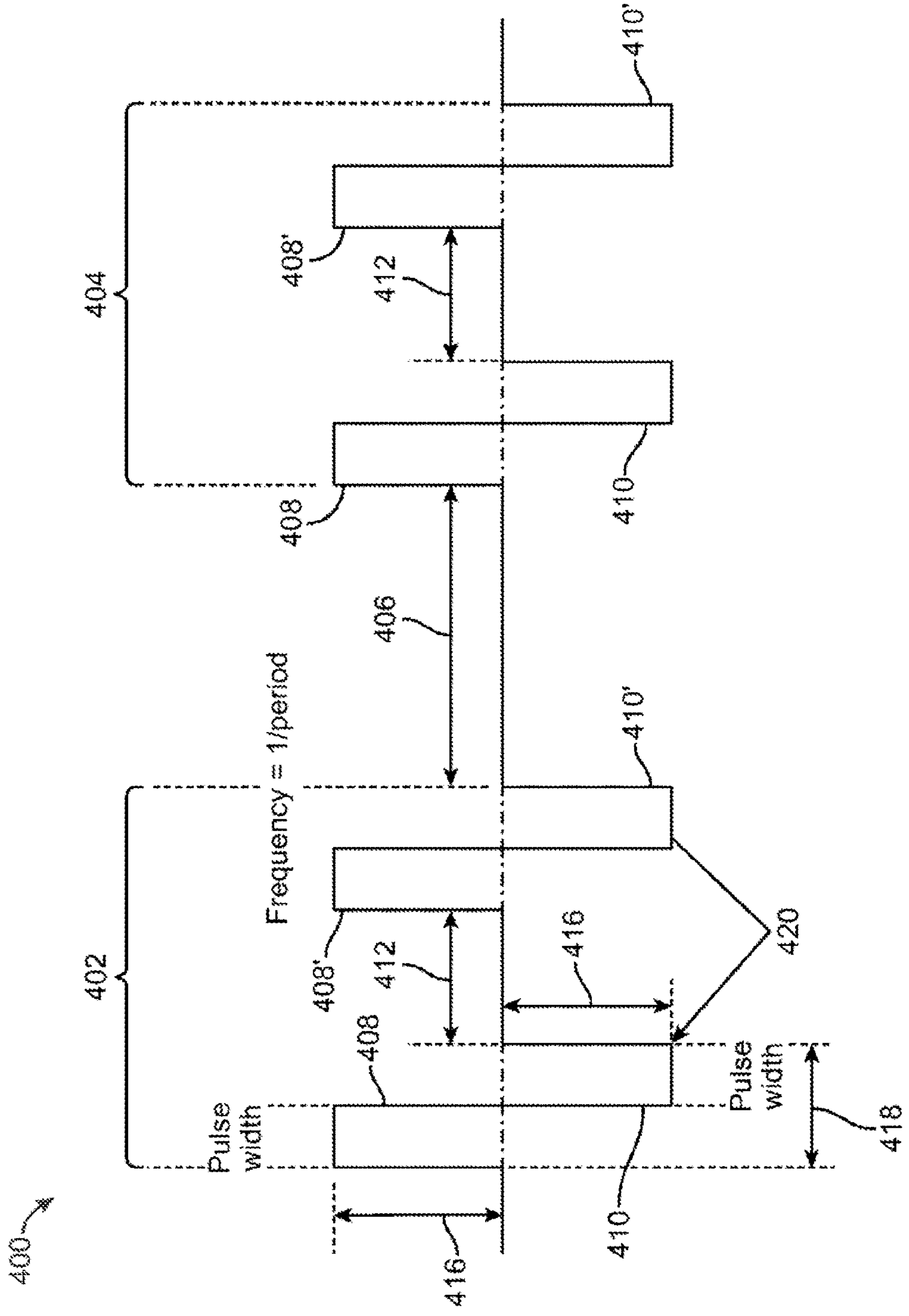
FIG. 9 illustrates an embodiment of a waveform of a signal prescribed by an energy delivery algorithm.

FIG. 9 illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e. a pause) between each biphasic cycle. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 3500 V to 4000 V, about 3500 V to 5000 V, about 3500 V to 6000 V, including all values and subranges in between including about 250 V, 500 V, 1000 V, 1500 V, 2000V, 2500 V, 3000 V, 3500 V, 4000 V, 4500 V, 5000 V, 5500 V, 6000 V to name a few. Voltages delivered to the tissue may be based on the setpoint on the generator 104 while either taking in to account the electrical losses along the length of the device 102 due to inherent impedance of the device 102 or not taking in to account the losses along the length, i.e., delivered voltages can be measured at the generator or at the tip of the instrument.

It may be appreciated that the set voltage 416 may vary depending on whether the energy is delivered in a monopolar or bipolar fashion. In bipolar delivery, a lower voltage may be used due to the smaller, more directed electric field. The bipolar voltage selected for use in therapy is dependent on the separation distance of the electrodes, whereas the monopolar electrode configurations that use one or more distant dispersive pad electrodes may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

It may be appreciated that in various embodiments the output is controlled or modified to achieve a desired current rather than voltage. In some embodiments, the energy is delivered in a monopolar fashion and has a current of 20 amps, 21 amps, 22 amps, 23, amps, 24 amps, 25 amps, 26 amps, 27 amps, 28 amps, 29 amps, 30 amps, 31 amps, 32 amps, 33 amps, 34 amps or 35 amps to name a few.

B. Frequency

It may be appreciated that the number of biphasic cycles per second of time is the frequency when a signal is continuous. In some embodiments, biphasic pulses are utilized to reduce undesired muscle stimulation, particularly cardiac muscle stimulation. In other embodiments, the pulse waveform is monophasic and there is no clear inherent frequency. Instead, a fundamental frequency may be considered by doubling the monophasic pulse length to derive the frequency. In some embodiments, the signal has a frequency in the range 50 kHz-1 MHz, more particularly 50 kHz-1000 kHz. It may be appreciated that at some voltages, frequencies at or below 100-250 kHz may cause undesired muscle stimulation. Therefore, in some embodiments, the signal has a frequency in the range of 300-800 kHz, 400-800 kHz or 500-800 kHz, such as 300 kHz, 400 kHz, 450 kHz, 500 kHz, 550 kHz, 600 kHz, 650 kHz, 700 kHz, 750 kHz, 800 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 600 kHz, while in other cases the treatment may be delivered using 2000 V with a waveform frequency of 400 kHz.

D. Packets

As mentioned, the algorithm 152 typically prescribes a signal having a waveform comprising a series of energy packets wherein each energy packet comprises a series of high voltage pulses. The cycle count 420 is half the number of pulses within each biphasic packet. Referring to FIG. 9, the first packet 402 has a cycle count 420 of two (i.e. four biphasic pulses). In some embodiments, the cycle count 420 is set between 2 and 1000 per packet, including all values and subranges in between. In some embodiments, the cycle count 420 is 5-1000 per packet, 2-10 per packet, 2-20 per packet, 2-25 per packet, 10-20 per packet, 20 per packet, 20-30 per packet, 25 per packet, 20-40 per packet, 30 per packet, 30-45 per packet, 45 per packet, 20-50 per packet, 30-60 per packet, up to 60 per packet, up to 80 per packet, up to 100 per packet, up to 1,000 per packet or up to 2,000 per packet, including all values and subranges in between.

The packet duration is determined by the cycle count, among other factors. For a matching pulse duration (or sequence of positive and negative pulse durations for biphasic waveforms), the higher the cycle count, the longer the packet duration and the larger the quantity of energy delivered. In some embodiments, packet durations are in the range of approximately 50 to 1000 microseconds, such as 50 μs, 60 μs, 70 μs, 80 μs, 90 μs, 100 μs, 125 μs, 150 μs, 175 μs, 200 μs, 250 μs, 100 to 250 μs, 150 to 250 μs, 200 to 250 μs, 500 to 1000 μs to name a few. In other embodiments, the packet durations are in the range of approximately 100 to 1000 microseconds, such as 150 μs, 200 μs, 250 μs, 500 μs, or 1000 μs.

The number of packets delivered during treatment, or packet count, typically includes 1 to 250 packets including all values and subranges in between. In some embodiments, the number of packets delivered during treatment comprises 2-5 packets, 3 packets, 5 packets, 5-10 packets, 10 packets, 12 packets, 10-15 packets, 15 packets, 20 packets, 15-20 packets, 25 packets, 30 packets or greater than 30 packets.

E. Rest Period

In some embodiments, the time between packets, referred to as the rest period 406, is set between about 0.001 seconds and about 5 seconds, including all values and subranges in between. In other embodiments, the rest period 406 ranges from about 0.01-0.1 seconds, including all values and subranges in between. In some embodiments, the rest period 406 is approximately 0.5 ms-500 ms, 1-250 ms, or 10-100 ms to name a few.

F. Batches

In some embodiments, the signal is synced with the cardiac rhythm so that each packet is delivered synchronously within a designated period relative to the heartbeats, thus the rest periods coincide with the heartbeats. It may be appreciated that the packets that are delivered within each designated period relative to the heartbeats may be considered a batch or bundle. Thus, each batch has a desired number of packets so that at the end of a treatment period, the total desired number of packets have been delivered.

Each batch may have the same number of packets, however in some embodiments, batches have varying numbers of packets.

In some embodiments, only one packet is delivered between heartbeats. In such instances, the rest period may be considered the same as the period between batches. However, when more than one packet is delivered between batches, the rest time is typically different than the period between batches. In such instances, the rest time is typically much smaller than the period between batches. In some embodiments, each batch includes 1-10 packets, 1-5 packets, 1-4 packets, 1-3 packets, 2-3 packets, 2 packets, 3 packets, 4 packets 5 packets, 5-10 packets, to name a few. In some embodiments, each batch has a period of 0.5 ms-1 sec, 1 ms-1 sec, 10 ms-1 sec, 10 ms-100 ms, to name a few. In some embodiments, the period between batches is variable, depending on the heart rate of the patient. In some instances, the period between batches is 0.25-5 seconds.

Treatment of a tissue area ensues until a desired number of batches are delivered to the tissue area. In some embodiments, 2-50 batches are delivered per treatment, wherein a treatment is considered treatment of a particular tissue area. In other embodiments, treatments include 5-40 batches, 5-30 batches, 5-20 batches, 5-10 batches, 5 batches, 6 batches, 7 batches, 8 batches, 9 batches, 10 batches, 10-15 batches, etc.

G. Switch Time and Dead Time

A switch time, also known as inter-phase delay, is a delay or period of no energy that is delivered between the positive and negative peaks of a biphasic pulse, as illustrated in FIG. 9. In some embodiments, the switch time ranges between about 0 to about 1 microsecond, including all values and subranges in between. In other embodiments, the switch time ranges between 1 and 20 microseconds, including all values and subranges in between. In other embodiments, the switch time ranges between about 2 to about 8 microsecond, including all values and subranges in between.

Delays may also be interjected between each biphasic cycle, referred as "dead-time" or inter-pulse delay. Dead time occurs within a packet, but between biphasic pulses. This is in contrast to rest periods or inter-packet delays which occur between packets. In other embodiments, the dead time 412 is in a range of approximately 0 to 0.5 microseconds, 0 to 10 microseconds, 2 to 5 microseconds, 0 to 20 microseconds, about 0 to about 100 microseconds, or about 0 to about 100 milliseconds, including all values and subranges in between. In some embodiments, the dead time 412 is in the range of 0.2 to 0.3 microseconds. Dead time may also be used to define a period between separate, monophasic, pulses within a packet.

Delays, such as switch times and dead times, are introduced to a packet to reduce the effects of biphasic cancellation within the waveform. In some instances, the switch time and dead time are both increased together to strengthen the effect. In other instances, only switch time or only dead time are increased to induce this effect.

G. Waveforms

FIG. 9 illustrated an embodiment of a waveform 400 having symmetric pulses such that the voltage and duration of pulse in one direction (i.e., positive or negative) is equal to the voltage and duration of pulse in the other direction. It may be appreciated that in other embodiments the waveform 400 has voltage imbalance. For example, each packet 402, 404 may be comprised of a first biphasic cycle (comprising a first positive pulse peak 408 having a first voltage V1 and a first negative pulse peak 410 having a second voltage V2) and a second biphasic cycle (comprising a second positive pulse peak 408' having first voltage V1 and a second negative pulse peak 410' having a second voltage V2). Here the first voltage V1 is greater than the second voltage V2. The first and second biphasic cycles are separated by dead time 412 between each pulse. Thus, the voltage in one direction (i.e., positive or negative) is greater than the voltage in the other direction so that the area under the positive portion of the curve does not equal the area under the negative portion of the curve. This unbalanced waveform may result in a more pronounced treatment effect. It may be appreciated that in some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative) is greater than the duration of the other direction, so that the area under the curve of the positive portion of the waveform does not equal the area under the negative portion of the waveform.

It may be appreciated that although the detailed examples included herein are described in terms of PEF energy, aspects of the methods, systems and devices described herein may be applicable all energy sources (e.g. radiofrequency therapy, cryogenic therapy, laser therapy, etc.).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A cardiovascular lesion analysis system comprising:

an instrument configured to measure at least one pre-ablation voltage value and at least one post-ablation voltage value of at least a portion of a cardiovascular lesion created by pulsed electric field ablation;

an algorithm that evaluates the at least one pre-ablation voltage value and the at least one post-ablation voltage value so as to determine durability of the at least a portion of the cardiovascular lesion by determining a representative voltage reduction value from a difference between the at least one pre-ablation voltage value and the at least one post-ablation voltage value; and a feedback system that conveys the durability.

2. A system as in claim 1, wherein the at least one voltage value comprises at least one pre-ablation voltage value and at least one post-ablation voltage value and wherein the algorithm evaluates the at least one voltage value by determining a representative voltage reduction value from the difference between the at least one pre-ablation voltage value and at least one post-ablation voltage value, and wherein the algorithm determines the likelihood of durability based on the representative voltage reduction value.

3. A system as in claim 2, wherein the pre-ablation voltage value is at least 0.1 volts.

4. A system as in claim 2, wherein the pre-ablation voltage value comprises an average of individual pre-ablation voltage values and the post-ablation voltage value comprises an average of individual post-ablation voltage values.

5. A system as in claim 4, wherein each of the individual pre-ablation voltage values are at least 0.1 volts.

6. A system as in claim 2, wherein the algorithm compares the representative reduction value to a threshold voltage reduction value above which the lesion is considered durable so as to determine durability.

7. A system as in claim 6, wherein the representative voltage reduction value is represented as a percentage of the pre-ablation voltage value.

8. A system as in claim 7, wherein the threshold voltage reduction value is 89%.

9. A system as in claim 7, wherein the threshold voltage reduction value falls within a range of 89-100%.

10. A system as in claim 6, wherein the threshold voltage reduction value has at least a 95% confidence level.

11. A system as in claim 6, wherein the threshold voltage reduction value is dependent on a baseline voltage value.

12. A system as in claim 11, wherein the threshold voltage reduction value varies in discrete steps in relation to the baseline voltage value.

13. A system as in claim 11, wherein the threshold voltage reduction value varies continuously in relation to the baseline voltage value.

14. A system as in claim 11, wherein the threshold voltage reduction value varies with confidence level.

15. A system as in claim 1, wherein the feedback system conveys the durability as a continuous variable that changes over time.

16. A system as in claim 15, wherein the continuous variable is conveyed as percent reduction in voltage.

17. A system as in claim 16, wherein the feedback system additionally conveys a target percent reduction in voltage.

18. A system as in claim 1, wherein any of the instrument, algorithm and/or feedback system is integral with an electroanatomic mapping system.

19. A system as in claim 1, wherein the feedback system is integrated with a pre-existing visual map provided by the electroanatomic mapping system.

20. A system as in claim 1, wherein the feedback system conveys the durability by providing an alert.

21. A system as in claim 20, wherein the alert comprises a visual alert.

22. A system as in claim 21, wherein the visual alert comprises a color code indicating durability or a level of durability.

23. A system as in claim 21, wherein the visual alert comprises at least one letter, word, number and/or symbol indicating durability or a level of durability.

24. A system as in claim 21, wherein the alert comprises an auditory alert.

25. A system as in claim 21, wherein the alert is binary.

26. A system as in claim 21, wherein the alert is gradated.

27. A system as in claim 1, wherein the feedback system comprises a map illustrating an anatomical location of the at least a portion of the cardiovascular lesion.

28. A system as in claim 27, wherein the feedback system comprises an indicator of the durability of the at least a portion of the cardiovascular lesion at the anatomical location on the map.

29. A system as in claim 1, wherein the feedback system conveys the durability to a user in real-time as the instrument moves.

30. A system as in claim 1, wherein the instrument is configured to deliver the pulsed electric field energy.

31. A system as in claim 30, wherein the instrument comprises an electrode through which the pulsed electric field energy is delivered and wherein the electrode is configured to be positioned against or adjacent tissue to create the at least a portion of the cardiovascular lesion.

32. A system as in claim 31, wherein the at least a portion of the cardiovascular lesion is formed from a single application of the electrode against or adjacent the tissue, and wherein the algorithm determines a location for a next single application of the electrode.

33. A system as in claim 32, wherein the location for the next single application of the electrode overlaps the at least a portion of the cardiovascular lesion formed from the single application of the electrode.

34. A system as in claim 32, wherein the location for the next single application of the electrode provides sufficient overlap of stun zones between kill zones to form a continuous durable lesion.

35. A system as in claim 32, wherein the algorithm identifies an edge of the at least a portion of the cardiovascular lesion by evaluating a spatial distribution of a durability metric across tissue surrounding the at least a portion of the cardiovascular lesion and determining a boundary location at which the durability metric exhibits a drop-off relative to adjacent locations, and wherein the algorithm determines the location for the next single application of the electrode based at least in part on the boundary location.

36. A system as in claim 1, wherein the pulsed electric field energy leaves extracellular matrices of the cardiovascular lesion intact.

37. A system as in claim 1, wherein the pulsed electric field energy comprises a series of packets, wherein each packet comprises biphasic pulses.

38. A system for determining lesion placement comprising:

a catheter having an electrode configured to deliver pulsed electric field energy toward cardiovascular tissue so as to generate a lesion, wherein a first lesion is generated by delivering the pulsed electric field energy toward the cardiovascular tissue at a first location;

an algorithm that determines a second location for a second lesion based on a determined durability of the first lesion, wherein the determined durability of the first lesion is generated by the algorithm from a representative voltage reduction value calculated as a differential between a pre-ablation voltage value and a post-ablation voltage value of the first lesion; and a feedback system that conveys the second location.

39. A system as in claim 38, wherein the determined durability of the first lesion is generated by the algorithm by comparing a representative reduction value to a threshold voltage reduction value above which the first lesion is considered durable.

40. A system as in claim 39, wherein the representative voltage reduction value is calculated as a differential between a pre-ablation voltage value and a post-ablation voltage value.

41. A system as in claim 40, wherein the pre-ablation voltage value is at least 0.1 volts.

42. A system as in claim 40, wherein the pre-ablation voltage value comprises an average of individual pre-ablation voltage values and the post-ablation voltage value comprises an average of individual post-ablation voltage values.

43. A system as in claim 42, wherein each of the individual pre-ablation voltage values are at least 0.1 volts.

44. A system as in claim 40, wherein the representative voltage reduction value is represented as a percentage of the pre-ablation voltage value.

45. A system as in claim 44, wherein the threshold voltage reduction value is 89%.

46. A system as in claim 44, wherein the threshold voltage reduction value falls within a range of 89-100%.

47. A system as in claim 44, wherein the threshold voltage reduction value has at least a 95% confidence level.

48. A system as in claim 38, wherein the impedance of the cardiovascular tissue remains below a threshold corresponding to impedance generated by thermal ablation.

49. A system as in claim 38, wherein the pulsed electric field energy comprises a series of packets, wherein each packet comprises biphasic pulses.

50. A cardiovascular lesion analysis system comprising:

a catheter having at least one electrode; and a pulsed electric field generator connectable with the catheter, wherein the pulsed electric field generator includes an algorithm configured to deliver at least one dose of pulsed electric field energy through at least one of the at least one electrode to an area of cardiovascular tissue so as to create a lesion and to measure a pre-ablation voltage value and a post-ablation voltage value of at least a portion of the cardiovascular lesion through at least one of the at least one electrode, and wherein the algorithm determines durability of the at least a portion of the cardiovascular lesion from a representative voltage reduction value calculated as a difference between the pre-ablation voltage value and the post-ablation voltage value.

51. A system as in claim 50, wherein the at least one voltage value comprises a representative voltage reduction value, and wherein the algorithm compares the representative reduction value to a threshold voltage reduction value above which the lesion is considered durable so as to determine durability.

52. A system as in claim 51, wherein the representative voltage reduction value is represented as a percentage of a pre-ablation voltage value.

53. A system as in claim 52, wherein the threshold voltage reduction value is 89%.

54. A system as in claim 52, wherein the threshold voltage reduction value falls within a range of 89-100%.

55. A system as in claim 52, wherein the pre-ablation voltage value is at least 0.1 volts.

56. A system as in claim 52, wherein the pre-ablation voltage value comprises an average of individual pre-ablation voltage values.

57. A system as in claim 56, wherein each of the individual pre-ablation voltage values are at least 0.1 volts.

58. A system as in claim 51, wherein the threshold voltage reduction value has at least a 95% confidence level.

59. A system as in claim 50, wherein the pulsed electric field energy leaves extracellular matrices of the cardiovascular lesion intact.

60. A system as in claim 50, wherein the pulsed electric field energy comprises a series of packets, wherein each packet comprises biphasic pulses.

61. A system as in claim 50, wherein the algorithm provides the durability to a visual map that includes the area of cardiovascular tissue.

62. A system as in claim 61, wherein the visual map is provided by an electroanatomic mapping system.

63. A system as in claim 61, wherein the visual map illustrates an anatomical location of the at least a portion of the cardiovascular lesion.

64. A system as in claim 63, wherein the feedback system comprises an indicator of the durability of the at least a portion of the cardiovascular lesion at the anatomical location on the map.

65. A system as in claim 50, wherein the algorithm provides the durability as an alert.

66. A cardiovascular lesion analysis system for intraoperative durability assessment of a pulsed electric field ablation lesion, comprising:

an instrument configured to measure at least one pre-ablation voltage value and at least one post-ablation voltage value of at least a portion of a cardiovascular lesion created by pulsed electric field ablation during an ablation procedure;

an algorithm that evaluates the at least one pre-ablation voltage value and the at least one post-ablation voltage value to determine a representative voltage reduction value from a difference between the at least one pre-ablation voltage value and the at least one post-ablation voltage value, wherein the representative voltage reduction value is represented as a percentage of the pre-ablation voltage value, and wherein the algorithm classifies the at least a portion of the cardiovascular lesion as durable if the representative voltage reduction value is greater than or equal to 89% and classifies the at least a portion of the cardiovascular lesion as non-durable if the representative voltage reduction value is less than 89%, wherein said classification distinguishes between tissue permanently killed by the pulsed electric field ablation and tissue transiently stunned by the pulsed electric field ablation; and a feedback system that conveys the durability classification during the ablation procedure.

* * * * *